(12) United States Patent
Wang et al.

(10) Patent No.: US 10,739,430 B2
(45) Date of Patent: Aug. 11, 2020

(54) SYSTEM AND METHOD FOR DETERMINING FLIP ANGLES IN MAGNETIC RESONANCE IMAGING

(71) Applicant: SHANGHAI UNITED IMAGING HEALTHCARE CO., LTD., Shanghai (CN)

(72) Inventors: Chaohong Wang, Shanghai (CN); Guobin Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 414 days.

(21) Appl. No.: 15/692,148

(22) Filed: Aug. 31, 2017

(65) Prior Publication Data

US 2019/0064295 A1 Feb. 28, 2019

(30) Foreign Application Priority Data

Aug. 28, 2017 (CN) .......................... 2017 1 0752718

(51) Int. Cl.
*G01R 33/54* (2006.01)
*G01R 33/561* (2006.01)
(Continued)

(52) U.S. Cl.
CPC ............ *G01R 33/543* (2013.01); *A61B 5/055* (2013.01); *G01R 33/5617* (2013.01); *G01R 33/288* (2013.01); *G01R 33/4808* (2013.01)

(58) Field of Classification Search
CPC .............. G01R 33/543; G01R 33/5617; G01R 33/288; G01R 33/4808; A61B 5/055
(Continued)

(56) References Cited

U.S. PATENT DOCUMENTS 6,272,369 B1 * 8/2001 Tan ..................... G01R 33/4828
324/307
6,492,809 B1 * 12/2002 Speier ..................... G01V 3/32
324/303

(Continued)

FOREIGN PATENT DOCUMENTS

JP 2001299724 A 10/2001

OTHER PUBLICATIONS

Busse ["Effects of Refocusing Flip Angle Modulation and View Ordering in 3D Fast Spin Echo" Magnetic Resonance in Medicine. Sep. 2008, 60(3): 640-649] (Year: 2008).*

(Continued)

*Primary Examiner* — Oommen Jacob
(74) *Attorney, Agent, or Firm* — Metis IP LLC

(57) ABSTRACT

A method may include providing an initial flip angle schedule of refocusing radio frequency pulses, the refocusing radio frequency pulses being configured to generate an echo train; comparing the initial flip angle schedule with a first criterion, the first criterion relating to a first parameter relating to the echo train; determining, a first flip angle schedule based on the first comparison, the first flip angle schedule satisfying the first criterion; comparing the first flip angle schedule with a second criterion, the second criterion relating to a second parameter relating to the echo train; determining, a second flip angle schedule based on the second comparison, the second flip angle schedule satisfying the second criterion; and obtaining a magnetic resonance (MR) signal based on the second flip angle schedule.

20 Claims, 14 Drawing Sheets

(51) Int. Cl.
*A61B 5/055* (2006.01)
*G01R 33/48* (2006.01)
*G01R 33/28* (2006.01)

(58) Field of Classification Search
USPC .......................................................... 600/407
See application file for complete search history.

(56) References Cited

U.S. PATENT DOCUMENTS

| | | | | |
|---|---|---|---|---|
| 6,956,374 B2* | 10/2005 | Busse | ................ | G01R 33/5613 |
| | | | | 324/314 |
| 8,072,212 B2* | 12/2011 | Park | ................... | G01R 33/4828 |
| | | | | 324/307 |
| 10,324,153 B2* | 6/2019 | Li | .......................... | A61B 5/055 |
| 10,429,477 B2* | 10/2019 | Li | ...................... | G01R 33/5615 |
| 2003/0042905 A1* | 3/2003 | Miyazaki | ........... | G01R 33/5635 |
| | | | | 324/314 |
| 2003/0234647 A1* | 12/2003 | Beaudoin | ............. | G01R 33/446 |
| | | | | 324/300 |
| 2004/0051527 A1* | 3/2004 | Mugler, III | ........ | G01R 33/5615 |
| | | | | 324/309 |
| 2005/0001617 A1* | 1/2005 | Busse | ................ | G01R 33/5613 |
| | | | | 324/307 |
| 2007/0161890 A1* | 7/2007 | Hariharan | .......... | G01R 33/5615 |
| | | | | 600/410 |
| 2008/0278159 A1* | 11/2008 | Park | ................... | G01R 33/5615 |
| | | | | 324/307 |
| 2008/0284439 A1* | 11/2008 | Xu | ........................ | A61B 5/055 |
| | | | | 324/322 |
| 2008/0319301 A1* | 12/2008 | Busse | .................... | A61B 5/055 |
| | | | | 600/410 |
| 2010/0013479 A1* | 1/2010 | Park | ....................... | G01R 33/54 |
| | | | | 324/309 |
| 2011/0181282 A1* | 7/2011 | Dannels | ............. | G01R 33/5617 |
| | | | | 324/309 |
| 2012/0235684 A1 | 9/2012 | Stemmer | | |
| 2012/0237100 A1* | 9/2012 | Grimm | .............. | G01R 33/5608 |
| | | | | 382/131 |
| 2014/0077805 A1* | 3/2014 | Hoshino | ............ | G01R 33/5617 |
| | | | | 324/307 |
| 2014/0084918 A1* | 3/2014 | Kurokawa | ......... | G01R 33/5617 |
| | | | | 324/307 |
| 2014/0210467 A1 | 7/2014 | Hwang et al. | | |
| 2015/0168524 A1* | 6/2015 | Nittka | .............. | G01R 33/56536 |
| | | | | 324/309 |
| 2016/0109548 A1* | 4/2016 | Lee | ........................ | A61B 5/055 |
| | | | | 324/309 |
| 2017/0212197 A1 | 7/2017 | Li et al. | | |
| 2019/0064295 A1* | 2/2019 | Wang | .................. | G01R 33/543 |

OTHER PUBLICATIONS

Busse2004 ["Reduced RF Power Without Blurring: Correcting for Modulation of Refocusing Flip Angle in FSE Sequences" Magnetic Resonance in Medicine 51:1031-1037 (2004)]. (Year: 2004).*

Search Report in European Application No. 17204380.4 dated Jul. 3, 2018, 17 pages.

Andreas M. Loening et al., Increased speed and image quality in single-shot fast spin echo imaging via variable refocusing flip angles, Journal of Magnetic Resonance Imaging, 42(6): 1747-1758 (2015).

Reed F. Busse et al., Effects of refocusing flip angle modulation and view ordering in 3D fast spin echo, Magnetic Resonance in Medicine, 60: 640-649 (2008).

Reed F. Busse et al., Fast spin echo sequences with very long echo trains: design of variable refocusing flip angle schedules and generation of clinical T2 contrast, Magnetic Resonance in Medicine, 55: 1030-1037 (2006).

International Search Report in PCT/CN2017/114107 dated May 25, 2018, 4 pages.

Written Opinion in PCT/CN2017/114107 dated May 25, 2018, 3 pages.

* cited by examiner

SYSTEM AND METHOD FOR DETERMINING FLIP ANGLES IN MAGNETIC RESONANCE IMAGING

CROSS-REFERENCE OF RELATED APPLICATIONS

This application claims priority of Chinese Patent Application No. 201710752718.X, filed on Aug. 28, 2017, the contents of which are hereby incorporated by reference.

TECHNICAL FIELD

The present disclosure generally relates to a magnetic resonance imaging (MRI) system, and more particularly, methods and systems for determining a target flip angle schedule.

BACKGROUND

Magnetic resonance imaging (MRI) systems are widely used to diagnose and treat medical conditions by exploiting a powerful magnetic field and radio frequency (RF) techniques. The radio frequency (RF) techniques make use of an excitation RF pulse and multiple refocusing RF pulses with specific flip angles to obtain MR signals for reconstructing MR images. In some embodiments, the multiple refocusing RF pulses may have the same flip angle or variable flip angles. However, a large number of refocusing RF pulses with the same large flip angle (e.g., also referred to as high-frequency RF pulses) may increase the high-frequency power deposition or specific absorption rate (SAR). The refocusing RF pulses with variable flip angles may decrease a signal-to-noise ratio and/or a contrast ratio in an MR image. Thus, it may be desirable to provide systems and methods for determining a target flip angle schedule of multiple refocusing RF pulses, which may decrease SAR and increase a signal-to-noise ratio and/or a contrast ratio simultaneously.

SUMMARY

According to an aspect of the present disclosure, a method for determining a target flip angle schedule is provided. The method may be implemented on at least one machine each of which has at least one processor and storage. The method may include providing an initial flip angle schedule of refocusing radio frequency pulses, the refocusing radio frequency pulses being configured to generate an echo train; comparing the initial flip angle schedule with a first criterion, the first criterion relating to a first parameter relating to the echo train; determining, a first flip angle schedule based on the first comparison, the first flip angle schedule satisfying the first criterion; comparing the first flip angle schedule with a second criterion, the second criterion relating to a second parameter relating to the echo train; determining, a second flip angle schedule based on the second comparison, the second flip angle schedule satisfying the second criterion; and obtaining a magnetic resonance (MR) signal based on the second flip angle schedule.

In some embodiments, the providing the initial flip angle schedule of the refocusing radio frequency pulses may include selecting an initial condition relating to the refocusing radio frequency pulses, the initial condition including initial values of a first flip angle and a second flip angle; and determining the initial flip angle schedule based on the initial values of the first flip angle and the second flip angle.

In some embodiments, the method may further include providing a function corresponding to at least a portion of the echo train, the function relating to at least one of the first flip angle and the second flip angle; and determining, based on the function, at least one flip angle of at least one refocusing radio frequency pulse, a flip angle of the at least one refocusing radio frequency pulse corresponding to an echo in the echo train.

In some embodiments, the first parameter may relate to the echo train includes an intensity value of at least one echo in the echo train.

In some embodiments, the determining, based on the first comparison, a first flip angle schedule may further include determining that the initial flip angle schedule does not satisfy the first criterion; adjusting, in response to the determination that the initial flip angle schedule does not satisfy, the initial flip angle schedule to determine the first flip angle schedule.

In some embodiments, the determining that the initial flip angle schedule does not satisfy a first criterion may include determining, based on the initial flip angle schedule, a first signal evolution; and determining that the initial flip angle schedule does not satisfy the first criterion by determining that the first signal evolution does not satisfy the first criterion. In some embodiments, the first signal evolution may include intensity values of at least a portion of echoes in the echo train.

In some embodiments, the first signal evolution may relate to a transverse relaxation time or longitudinal relaxation time.

In some embodiments, the first criterion may include a first threshold corresponding to the first signal evolution. In some embodiments, the determining that the initial flip angle schedule does not satisfy a first criterion may include determining that a maximum intensity value in the first signal evolution is lower than the first threshold.

In some embodiments, the first parameter relating to the echo train may include a total energy of the refocusing radio frequency pulses with the initial flip angel schedule.

In some embodiments, the determining that the initial flip angle schedule does not satisfy a first criterion may include determining, based on the initial flip angle schedule, the total energy of the refocusing radio frequency pulses; and evaluating the total energy of the refocusing radio frequency pulses according to the first criterion.

In some embodiments, the first criterion may include a second threshold corresponding to the total energy of the refocusing radio frequency pulses. In some embodiments, the determining that the initial flip angle schedule does not satisfy a first criterion may include determining that the total energy of the refocusing radio frequency pulses equals to or exceeds the second threshold.

In some embodiments, the determining, based on the second comparison, a second flip angle schedule, may further include determining that the first flip angle schedule does not satisfy the second criterion; and adjusting, in response to the determination that the first flip angle schedule does not satisfy a second criterion, the first flip angle schedule to determine a second flip angle schedule.

In some embodiments, the second parameter may include an equivalent echo time of the echo train corresponding to the first flip angle schedule.

In some embodiments, the second criterion may include a third threshold corresponding to the equivalent echo time of the echo train corresponding to the first flip angle schedule.

In some embodiments, the determining that the first flip angle schedule does not satisfy a second criterion may include determining a second signal evolution, the second signal evolution including intensity values of at least a portion of echoes in the echo train corresponding to the first flip angle schedule; determining, based on the second signal evolution, the equivalent echo time of the echo train corresponding to the first flip angle schedule; and determining that the first flip angle schedule does not satisfy the second criterion by determining that the second signal evolution does not satisfy the second criterion.

In some embodiments, the determining that the first flip angle schedule does not satisfy the second criterion may include determining that the equivalent echo time of the echo train corresponding to the first flip angle schedule is lower than the third threshold.

In some embodiments, the obtaining, based on the second flip angle schedule, a magnetic resonance (MR) signal may further include determining a target flip angle schedule based on the second flip angle schedule, including assessing the second flip angle schedule according to the first criterion; and adjusting, based on the assessing of the second flip angle schedule, the second flip angle schedule to determine the target flip angle schedule, the target flip angle schedule satisfying the first criterion and the second criterion.

In some embodiments, the determining, based on the first comparison, a first flip angle schedule may further include determining that the initial flip angle schedule satisfies the first criterion; and determining the initial flip angle schedule as the first flip angle schedule.

In some embodiments, the determining, based on the second comparison, a second flip angle schedule may further include determining that the first flip angle schedule satisfies the second criterion; and determining the first flip angle schedule as the second flip angle schedule.

According to an aspect of the present disclosure, a system for determining a target flip angle schedule is provided. The system may include at least one processor and executable instructions. When the executable instructions are executed by the at least one processor, the instructions may cause the system to implement a method. The method may include providing an initial flip angle schedule of refocusing radio frequency pulses, the refocusing radio frequency pulses being configured to generate an echo train; comparing the initial flip angle schedule with a first criterion, the first criterion relating to a first parameter relating to the echo train; determining, a first flip angle schedule based on the first comparison, the first flip angle schedule satisfying the first criterion; comparing the first flip angle schedule with a second criterion, the second criterion relating to a second parameter relating to the echo train; determining, a second flip angle schedule based on the second comparison, the second flip angle schedule satisfying the second criterion; and obtaining a magnetic resonance (MR) signal based on the second flip angle schedule.

According to another aspect of the present disclosure, a non-transitory computer readable medium is provided. The non-transitory computer readable medium may include executable instructions. When the instructions are executed by at least one processor, the instructions may cause the at least one processor to implement a method. The method may include providing an initial flip angle schedule of refocusing radio frequency pulses, the refocusing radio frequency pulses being configured to generate an echo train; comparing the initial flip angle schedule with a first criterion, the first criterion relating to a first parameter relating to the echo train; determining, a first flip angle schedule based on the first comparison, the first flip angle schedule satisfying the first criterion; comparing the first flip angle schedule with a second criterion, the second criterion relating to a second parameter relating to the echo train; determining, a second flip angle schedule based on the second comparison, the second flip angle schedule satisfying the second criterion; and obtaining a magnetic resonance (MR) signal based on the second flip angle schedule.

According to an aspect of the present disclosure, a system for determining a target flip angle schedule is provided. The system may include a data processing module configured to provide an initial flip angle schedule of refocusing radio frequency pulses, the refocusing radio frequency pulses being configured to generate an echo train; compare the initial flip angle schedule with a first criterion, the first criterion relating to a first parameter relating to the echo train; determine, based on the first comparison, a first flip angle schedule, the first flip angle schedule satisfying the first criterion; compare the first flip angle schedule with a second criterion, the second criterion relating to a second parameter relating to the echo train; and determine, based on the second comparison, a second flip angle schedule, the second flip angle schedule satisfying the second criterion The system may further include an acquisition module configured to obtain a magnetic resonance (MR) signal based on the second flip angle schedule.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 3:
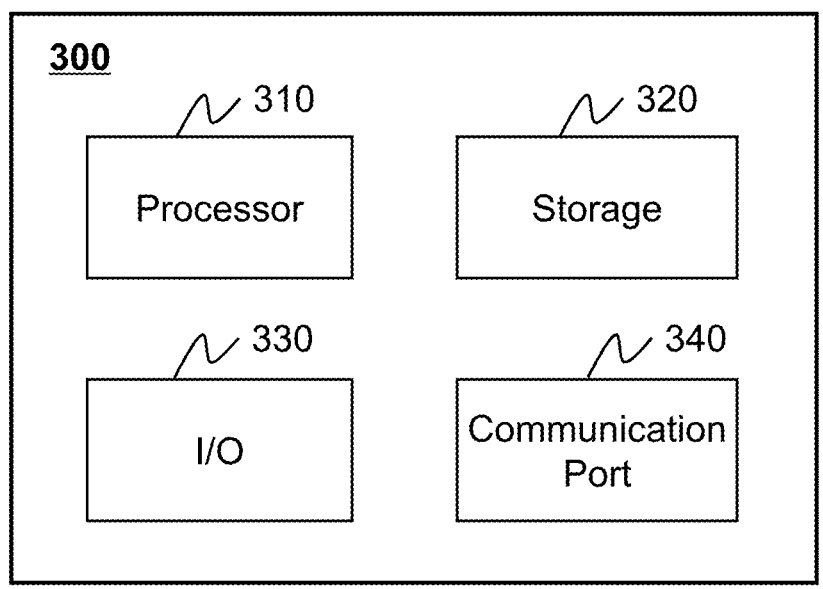
FIG. 3 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems and components for medical imaging. In some embodiments, the imaging system may include a single modality imaging system and/or a multi-modality imaging system. The single modality imaging system may include, for example, a magnetic resonance imaging (MRI) system. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc. It should be noted that the MRI system 100 described below is merely provided for illustration purposes, and not intended to limit the scope of the present disclosure.

An aspect of the present disclosure relates to systems and methods for determining a target flip angle schedule. In some embodiments, multiple refocusing RF pulses with the target flip angle schedule may be applied to at least a part of a subject being examined for generating MR signals. In some embodiments, the target flip angle schedule may be determined based on an initial flip angle schedule and one or more criteria (e.g., a desired value) relating to one or more parameters relating to the MR signals (e.g., an echo train). In some embodiments, the initial flip angle schedule may be assessed and/or adjusted based on the one or more criteria. For example, the initial flip angle schedule may be adjusted if the initial flip angle schedule does not satisfy the criteria to obtain the target flip angle that satisfies the one or more criteria.

Figure 1:
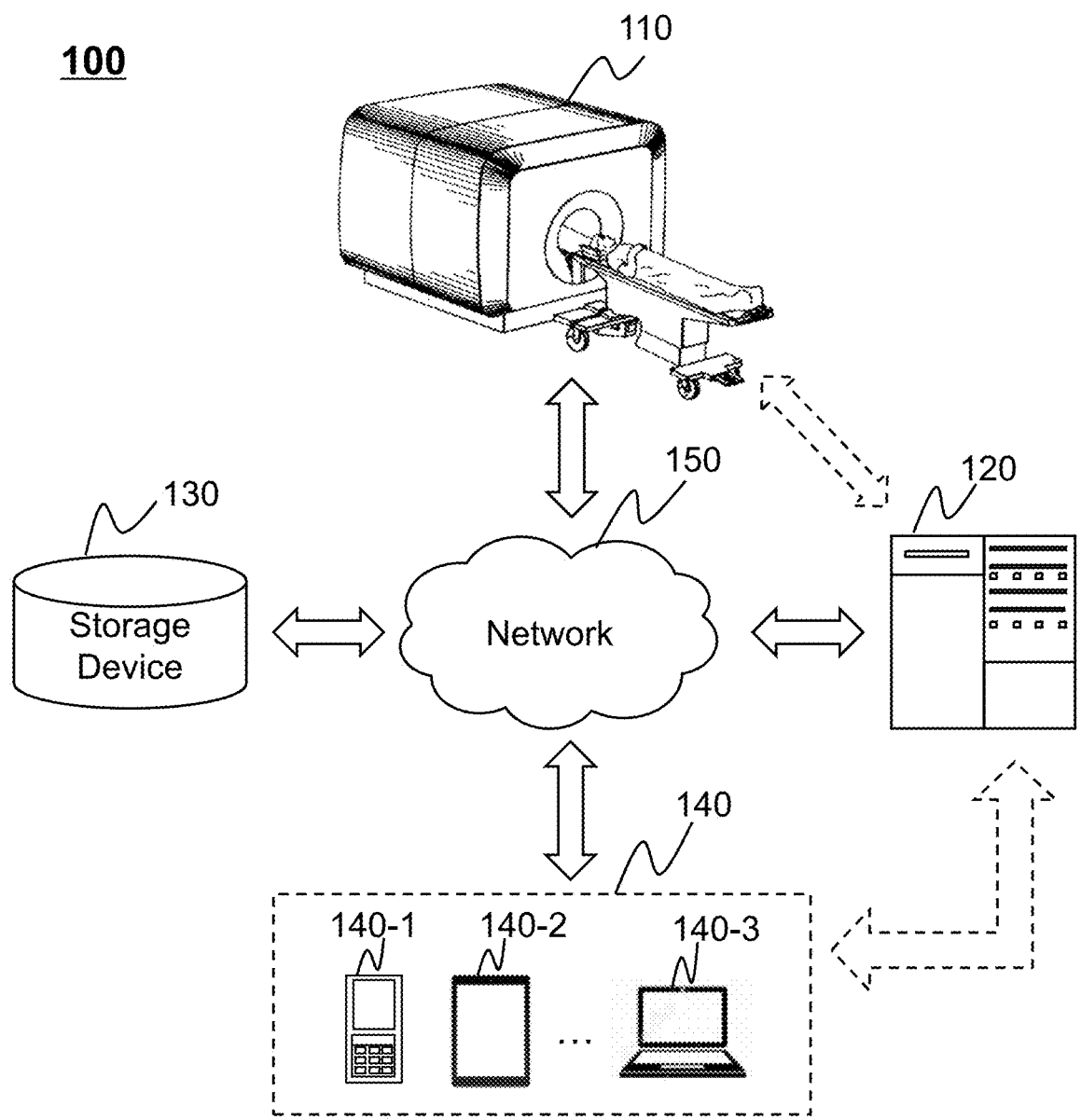
FIG. 1 is schematic diagram illustrating an exemplary MRI system according to some embodiments of the present disclosure.

FIG. 1 is schematic diagrams illustrating an exemplary MRI system 100 according to some embodiments of the present disclosure. As shown in FIG. 1, the MRI system 100 may include an MR scanner 110, a processing engine 120, a storage device 130, one or more terminals 140, and a network 150. In some embodiments, the MR scanner 110, the processing engine 120, the storage device 130, and/or the terminal(s) 140 may be connected to and/or communicate with each other via a wireless connection (e.g., the network 150), a wired connection, or a combination thereof. The connection between the components in the MRI system 100 may be variable. For example, the MR scanner 110 may be connected to the processing engine 120 through the network 150. As another example, the MR scanner 110 may be connected to the processing engine 120 directly.

The MR scanner 110 may generate or provide image data associated with MR signals via scanning a subject, or a part of the subject. In some embodiments, the MR scanner 110 may include, for example, a magnetic body 220, a gradient coil 230, a radio frequency (RF) coil 240, etc., as described in connection with FIG. 2. In some embodiments, the MR scanner 110 may be a permanent magnet MR scanner, a superconducting electromagnet MR scanner, or a resistive electromagnet MR scanner, etc., according to types of the magnetic body 220. In some embodiments, the MR scanner 110 may be a high-field MR scanner, a mid-field MR scanner, and a low-field MR scanner, etc., according to the intensity of the magnetic field.

The subject may be biological or non-biological. For example, the subject may include a patient, a man-made object, etc. As another example, the subject may include a specific portion, organ, and/or tissue of the patient. For example, the subject may include head, brain, neck, body, shoulder, arm, thorax, cardiac, stomach, blood vessel, soft tissue, knee, feet, or the like, or a combination thereof. In some embodiments, the MR scanner 110 may receive an MR signal related to the at least part of the subject.

The processing engine 120 may process data and/or information obtained from the MR scanner 110, the storage device 130, and/or the terminal(s) 140. For example, the processing engine 120 may generate an MR image by processing image data (e.g., MR signals) collected by the MR scanner 110. As another example, the processing engine 120 may determine one or more imaging parameters (e.g., a target flip angle schedule relating to refocusing RF pulses) based on, for example, a scanning protocol. In some embodiments, the processing engine 120 may be a single server or a server group. The server group may be centralized or distributed. In some embodiments, the processing engine 120 may be local or remote. For example, the processing engine 120 may access information and/or data from the MR scanner 110, the storage device 130, and/or the terminal(s) 140 via the network 150. As another example, the processing engine 120 may be directly connected to the MR scanner 110, the terminal(s) 140, and/or the storage device 130 to access information and/or data. In some embodiments, the processing engine 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing engine 120 may be implemented by a computing device 300 having one or more components as described in connection with FIG. 3.

The storage device 130 may store data, instructions, and/or any other information. In some embodiments, the storage device 130 may store data obtained from the processing engine 120 and/or the terminal(s) 140. In some embodiments, the storage device 130 may store data and/or instructions that the processing engine 120 may execute or use to perform exemplary methods described in the present disclosure. In some embodiments, the storage device 130 may include a mass storage, removable storage, a volatile read-and-write memory, a read-only memory (ROM), or the like, or a combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the MRI system 100 (e.g., the processing engine 120, the terminal(s) 140, etc.). One or more components of the MRI system 100 may access the data or instructions stored in the storage device 130 via the network 150. In some embodiments, the storage device 130 may be part of the processing engine 120.

The terminal(s) 140 may be connected to and/or communicate with the MR scanner 110, the processing engine 120, and/or the storage device 130. For example, the processing engine 120 may acquire a scanning from the terminal(s) 140. As another example, the terminal(s) 140 may obtain image data from the MR scanner 110, the processing engine 120, and/or the storage device 130. In some embodiments, the terminal(s) 140 may include a mobile device 140-1, a tablet computer 140-2, a laptop computer 140-3, or the like, or a combination thereof. For example, the mobile device 140-1 may include a mobile phone, a personal digital assistant (PDA), a gaming device, a navigation device, a point of sale (POS) device, a laptop, a tablet computer, a desktop, or the like, or a combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing engine 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing engine 120.

The network 150 may include any suitable network that can facilitate the exchange of information and/or data for the MRI system 100. In some embodiments, one or more components of the MRI system 100 (e.g., the MR scanner 110, the processing engine 120, the storage device 130, the terminal(s) 140, etc.) may communicate information and/or data with one or more other components of the MRI system 100 via the network 150. For example, the processing engine 120 may obtain image data (e.g., an MR signal) from the MR scanner 110 via the network 150. As another example, the processing engine 120 may obtain user instructions from the terminal(s) 140 via the network 150. The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 130 may be a data storage including cloud computing platforms, such as a public cloud, a private cloud, a community and hybrid cloud, etc. In some embodiments, the processing engine 120 may be integrated into the MR scanner 110. However, those variations and modifications do not depart the scope of the present disclosure.

Figure 2:
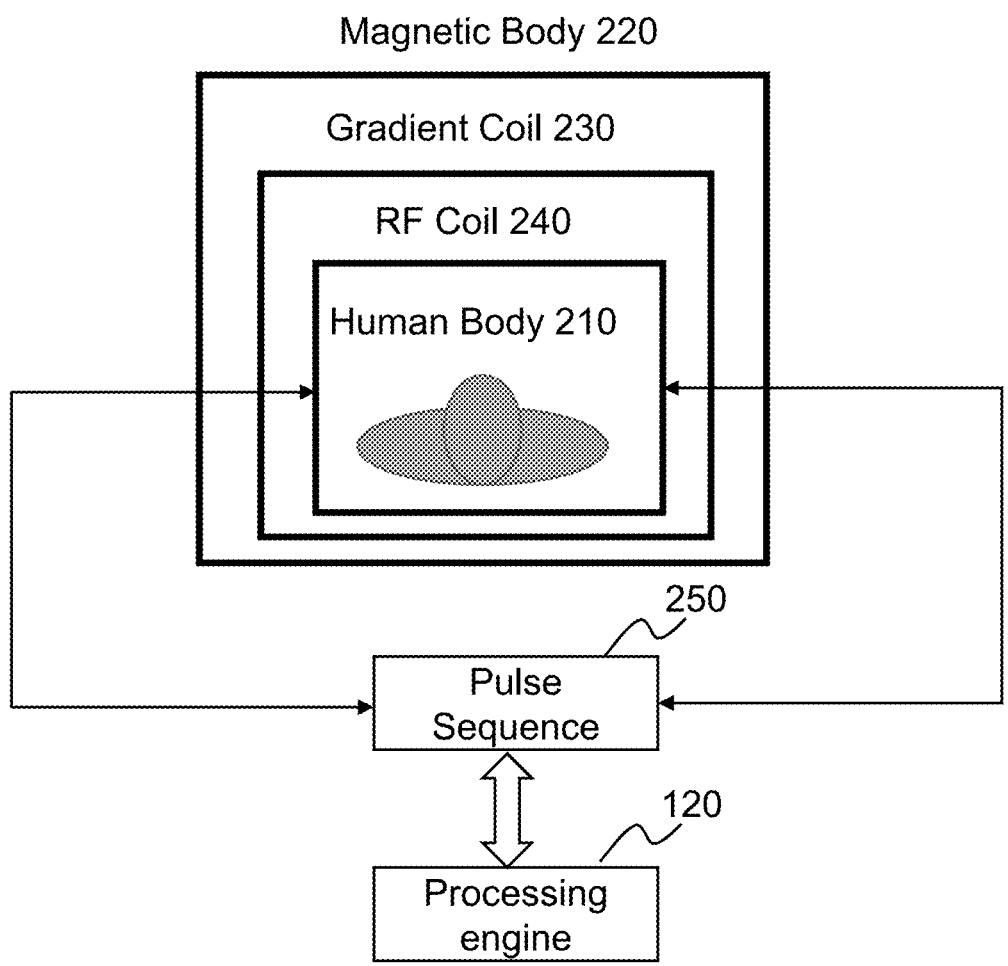
FIG. 2 is a block diagram illustrating an exemplary MR scanner according to some embodiments of the present disclosure.

FIG. 2 is a block diagram illustrating an exemplary MR scanner 110 according to some embodiments of the present disclosure. As illustrated in FIG. 2, the MR scanner 110 may include a magnetic body 220, a gradient coil 230, and a radio frequency (RF) coil 240 and a pulse sequence module 250.

The magnetic body 220 may generate a static magnetic field during the scanning of at least a part of a subject. The magnetic body 112 may be of various types including, for example, a permanent magnet, a superconducting electromagnet, a resistive electromagnet, etc.

The gradient coil 230 may provide magnetic field gradients to the main magnetic field in an X direction, a Y direction, and/or a Z direction. As used herein, the X direction, the Y direction, and the Z direction may represent an X axis, a Y axis, and a Z axis in a coordinate system. For example, the X axis and the Z axis may be in a horizontal plane, the X axis and the Y axis may be in a vertical plane, the Z axis may be along the axis of the magnetic body 112. In some embodiments, the gradient coil 230 may include an X-direction coil for providing a magnetic field gradient to the main magnetic field in the X direction, a Y-direction coil for providing a magnetic field gradient to the main magnetic field in the Y direction, and/or Z-direction coil for providing a magnetic field gradient to the main magnetic field in the Z direction. In some embodiments, the X-direction coil, the Y-direction coil, and/or the Z-direction coil may be of various shape or configuration. For example, the Z-direction coil may be designed based on a circular (Maxwell) coil. As another example, the X-direction coil and the Y-direction coil may be designed on the basis of a saddle (Golay) coil configuration.

The RF coil 240 may emit radio frequency (RF) pulse signals to and/or receive MR signals from a human body 210 being examined. In some embodiments, the RF coil 240 may include a transmitting coil and a receiving coil. The transmitting coil may emit signals (e.g., RF pulses) that may excite a nucleus in a subject (e.g., the human body 210) to provide a resonation. The receiving coil may receive MR signals emitted from the subject. In some embodiments, the RF transmitting coil and RF receiving coil may be integrated into the same coil. In some embodiments, the RF coil 240 may be of various types including, for example, a QD orthogonal coil, a phased-array coil, a specific element spectrum coil, etc.

In some embodiments, the RF coil 240 may generate a series of RF pulses periodically. For example, the RF coil 240 may generate an excitation RF pulse and a certain number of refocusing RF pulses. In some embodiments, the excitation RF pulse and the refocusing RF pulses may be defined by one or more parameters including, for example, a bandwidth (also referred to as a frequency range), an amplitude or strength, a time for applying a RF pulse, a duration for applying a RF pulse, a refocusing time (also referred to as a time interval between two RF pulses), a flip angle relating to a RF pulse, a number of RF pulses, etc. For example, the RF coil 240 may generate an excitation RF pulse with a flip angle of 90° and multiple refocusing RF pulses with a flip angle of 180°. Note that the excitation RF pulse may have a flip angle other than 90°, e.g., any magnitude ranging from 0° to 180°. The flip angle of a refocusing RF pulse may be of a value other than 180°. Furthermore, the RF coil 240 may generate a series of RF pulses periodically. For example, the RF coil 240 may generate an excitation RF pulse with a flip angle of 90° and multiple refocusing RF pulses with same flip angles or variable flip angles ranging from 0° to 180°. The flip angle of the excitation RF pulse may be variable as well.

In some embodiments, the excitation RF pulse may be utilized to generate a magnetic field corresponding to the gradient coil 230, and the multiple refocusing RF pulses may be configured to generate one or more MR signals (e.g., an echo train with multiple echoes). In some embodiments, a parameter relating to an MR signal may include, for example, a MR signal type (a spin echo, a fast spin echo (FSE), a fast recovery FSE, a single shot FSE, a gradient recalled echo, a fast imaging with steady-state precession, etc.), an echo number, an equivalent TE, an echo time (TE), a repetition time (TR), an echo train length (ETL), the number of phases, a signal intensity of an echo, etc. For example, a phase of an echo train may refer to a segment, section, part or fragment of an echo train and indicate a trend of echo signals in the echo train. The number of phase(s) and/or the number of echo(es) in each phase may depend on clinical demands. In some embodiments, an echo train may be divided into several phases (e.g., three phases). The multiple refocusing RF pulses corresponding to an echo train may be divided into several phases corresponding to the phases of the echo train. In some embodiments, the refocusing RF pulses in each phase may vary monotonically, for example, increase or decrease. The echo train length (ETL) may refer to the number of echoes in an echo train. The echo train length (ETL) may be either fixed or variable. For example, for the same tissue to be imaged, ETL may be fixed. For different tissues, ETL may be variable. Furthermore, even for the same tissue, ETL may be variable. The repetition time (TR) may refer to the time between the applications of two consecutive excitation RF pulses. The echo time (TE) may refer to the time between the middle of an excitation RF pulse and the middle of the spin echo production. As used herein, "middle" may refer to when the signal intensity of an echo corresponding to a pulse, e.g., an excitation RF pulse, a refocusing RF pulse, arrives at a maximum value. In some embodiments, for fast spin echo, as an echo corresponding to the central k-space line is the one that may determine image contrast, the time between the middle of an exciting RF pulse and the middle of the echoes corresponding to the central k-space (also referred to as a center echo) is called equivalent echo time (equivalent TE, or TEeff), also referred to as effective TE.

The pulse sequence module 250 may be defined by imaging parameters and arrangement in time sequence corresponding to the imaging parameters. In some embodiments, the imaging parameters may include parameters relating to an RF pulse (e.g., the number of excitations (NEX), a bandwidth, etc.) emitted by the RF coil 220, parameters relating to gradient fields generated by the gradients coil 230, and parameters relating to MR signals (e.g., an echo time (TE), an echo train length (ETL), a spin echo type, the number of phases) as described elsewhere in the disclosure. In some embodiments, the imaging parameter may include image contrast and/or ratio, a subject of interest, slice thickness, an imaging type (e.g., T1 weighted imaging, T2 weighted imaging, proton density weighted imaging, etc.), T1, T2, an acquisition time (TA), an inversion time, or the like, or a combination thereof. As used herein, T1 (i.e., longitudinal relaxation time) may be defined as the time needed for the longitudinal magnetization to reach (1-1/e) or about 63% of its maximum value. T2 (i.e., transverse relaxation time) may be defined as the time needed for the transverse magnetization to fall to 1/e or about 37% of its maximum value. It should be noted that for different subjects (e.g., tissues), their T1 and/or T2 are usually different from each other even when they are subject to the same magnet field. It should also be noted that T1 and T2 may be different from each other for the same tissue of the same subject under the same magnet filed. In some embodiments, the pulse sequence module 250 may include a spin echo sequence, a gradient echo sequence, a diffusion sequence, an inversion recovery sequence, or the like, or a combination thereof. For example, the spin echo sequence may include a fast spin echo (FSE), a turbo spin echo (TSE), a rapid acquisition with relaxation enhancement (RARE), a half-Fourier acquisition single-shot turbo spin-echo (HASTE), a turbo gradient spin echo (TGSE), or the like, or a combination thereof.

In some embodiments, the pulse sequence module 250 may be connected to and/or communicate with the processing engine 120. For example, before an MRI scanning process, at least one portion of the pulse sequence module 250 (e.g., parameters relating to RF pulses, parameters relating to gradient fields) may be designed and/or determined by the processing engine 120 according to clinical demands or a scanning protocol. In an MRI scanning process, the MR scanner 110 may scan a subject (e.g., the human body 210) based on the pulse sequence module 250. For example, the RF coil 240 may emit RF pulses with specific parameters relating to RF pulses of the pulse sequence module 250, and receive MR signals according to the pulse sequence module 250 (e.g., the echo time).

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the pulse sequence module 250 may be integrated into the processing engine 120. However, those variations and modifications do not depart the scope of the present disclosure.

FIG. 3 is a schematic diagram illustrating exemplary hardware and/or software components of an exemplary computing device 300 on which the processing engine 120 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (e.g., program code) and perform functions of the processing engine 120 in accordance with techniques described herein. The computer instructions may include, for example, routines, programs, objects, components, data structures, procedures, modules, and functions, which perform particular functions described herein. For example, the processor 310 may process image data obtained from the MR scanner 110, the storage device 130, terminal(s) 140, and/or any other component of the MRI system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the MR scanner 110, the storage device 130, the terminal(s) 140, and/or any other component of the MRI system 100. In some embodiments, the storage 320 may include a mass storage, removable storage, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing engine 120 for determining a target flip angle schedule.

The I/O 330 may input and/or output signals, data, information, etc. In some embodiments, the I/O 330 may enable a user interaction with the processing engine 120. In some embodiments, the I/O 330 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 340 may be connected to a network (e.g., the network 120) to facilitate data communications. The communication port 340 may establish connections between the processing engine 120 and the MR scanner 110, the storage device 130, and/or the terminal(s) 140. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
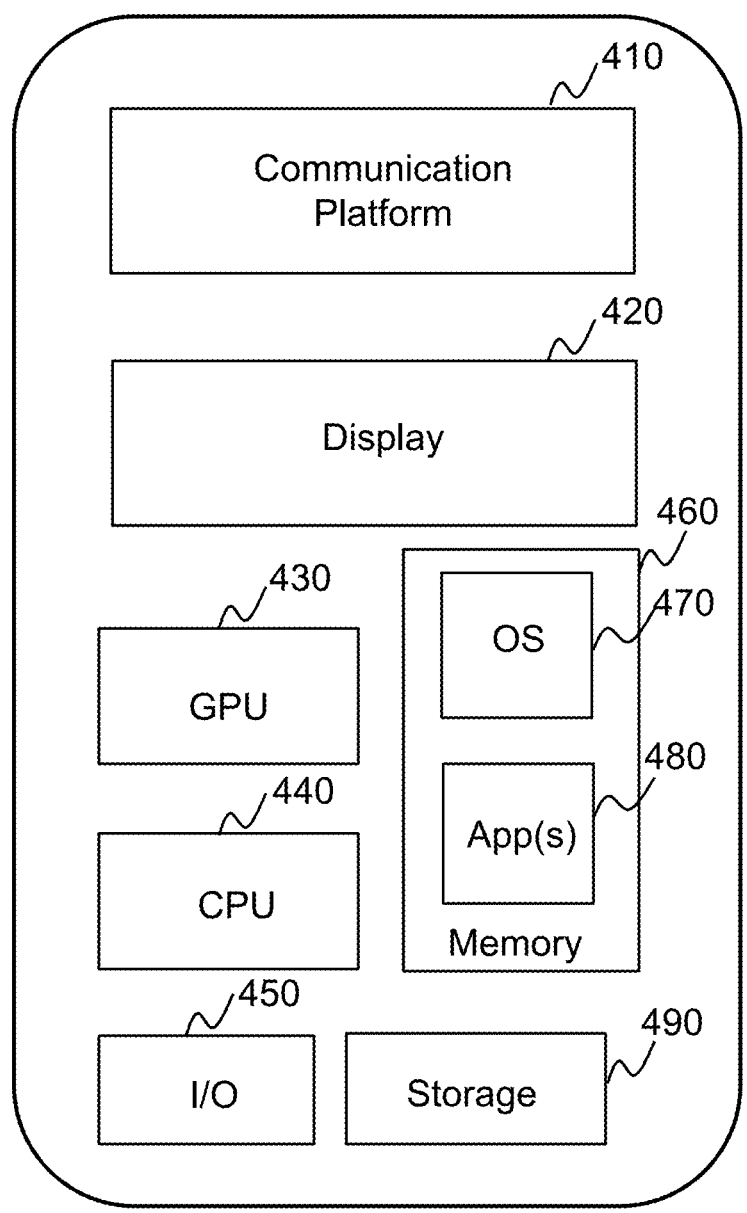
FIG. 4 is a schematic diagram illustrating exemplary hardware and/or software components of an exemplary mobile device according to some embodiments of the present disclosure.

FIG. 4 is a schematic diagram illustrating exemplary hardware and/or software components of an exemplary mobile device 400 on which the terminal(s) 140 may be implemented according to some embodiments of the present disclosure. As illustrated in FIG. 4, the mobile device 400 may include a communication platform 410, a display 420, a graphic processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing engine 120. User interactions with the information stream may be achieved via the I/O 450 and provided to the processing engine 120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
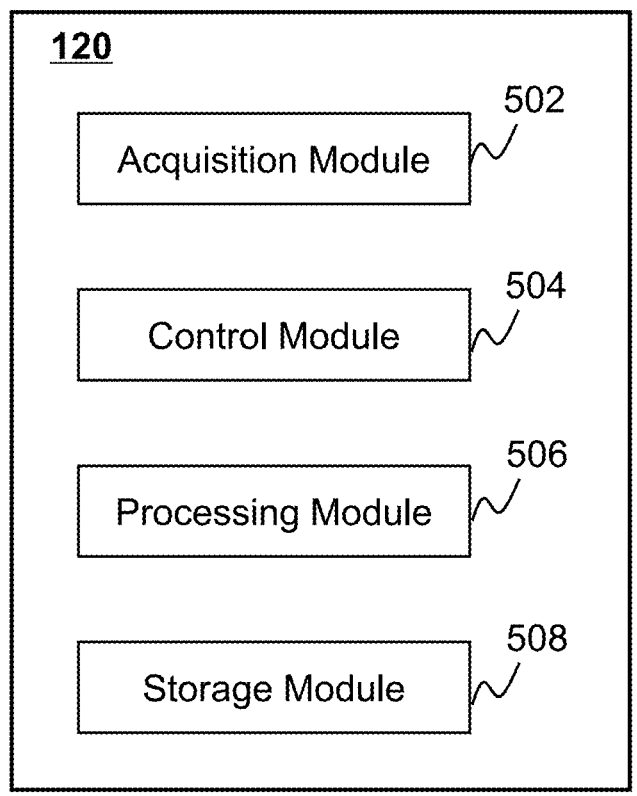
FIG. 5 is a block diagram illustrating an exemplary processing engine according to some embodiments of the present disclosure.

FIG. 5 is a block diagram illustrating an exemplary processing engine 120 according to some embodiments of the present disclosure. The processing engine 120 may include an acquisition module 502, a control module 504, a processing module 506, and a storage module 508. At least a portion of the processing engine 120 may be implemented on a computing device as illustrated in FIG. 3 or a mobile device as illustrated in FIG. 4.

The acquisition module 502 may acquire data. In some embodiments, the data may be acquired from the MR scanner 110, the storage device 130, and/or the terminal(s) 140. In some embodiments, the data may include a scanning protocol, at least one portion of imaging parameters as described elsewhere in the present disclosure, image data (e.g., MR signals, MR images), instructions, or the like, or a combination thereof. The instructions may be executed by the processor(s) of the processing engine 120 to perform exemplary methods described in the present disclosure. In some embodiments, the acquired data may be transmitted to the processing module 506 for further processing, or stored in the storage module 508.

The control module 504 may control operations of the acquisition module 502, the storage module 508, and/or the processing module 506 (e.g., by generating one or more control parameters). For example, the control module 504 may control the processing module 506 to process imaging parameters for determining a flip angle schedule of multiple refocusing RF pulses. As another example, the control module 504 may control the acquisition module 502 to acquire image data (e.g., an MR signal). As still another example, the control module 504 may control the processing module 506 to process MR signals to generate an MR image. In some embodiments, the control module 504 may receive a real-time command or retrieve a predetermined instruction provided by a user (e.g., a doctor) to control one or more operations of the acquisition module 502 and/or the processing module 506. For example, the control module 504 may adjust the acquisition module 502 and/or the processing module 506 to generate image data associated with the MR signals according to the real-time instruction and/or the predetermined instruction. In some embodiments, the control module 504 may communicate with one or more other modules of the processing engine 120 for exchanging information and/or data.

The processing module 506 may process data provided by various modules of the processing engine 120. In some embodiments, the processing module 506 may generate an MR image by processing MR signals acquired by the acquisition module 502, retrieved from the storage module 508 and/or the storage device 130, etc. In some embodiments, the processing module 506 may determine at least one portion of imaging parameters, such as a flip angel schedule of refocusing RF pulses according to, for example, a scanning protocol, a type of a subject being examined, etc.

The storage module 508 may store information. The information may include programs, software, algorithms, data, text, number, images, and some other information. For example, the information may include scanning protocols, imaging parameters, image data (e.g., MR signals, MR images, etc.), or the like, or a combination thereof. In some embodiments, the storage module 508 may store program(s) and/or instruction(s) that can be executed by the processor(s) of the processing engine 120 to acquire data, determine imaging parameters, reconstruct MR images, and/or display any intermediate result or a resultant image.

In some embodiments, one or more modules illustrated in FIG. 5 may be implemented in at least part of the exemplary MRI system 100 as illustrated in FIG. 1. For example, the acquisition module 502, the control module 504, the processing module 506, and/or the storage module 508 may be integrated into a console (not shown). Via the console, a user may set parameters for scanning a subject, controlling imaging processes, controlling parameters for reconstruction of an image, etc. In some embodiments, the console may be implemented via the processing engine 120 and/or the terminal(s) 140.

Figure 6:
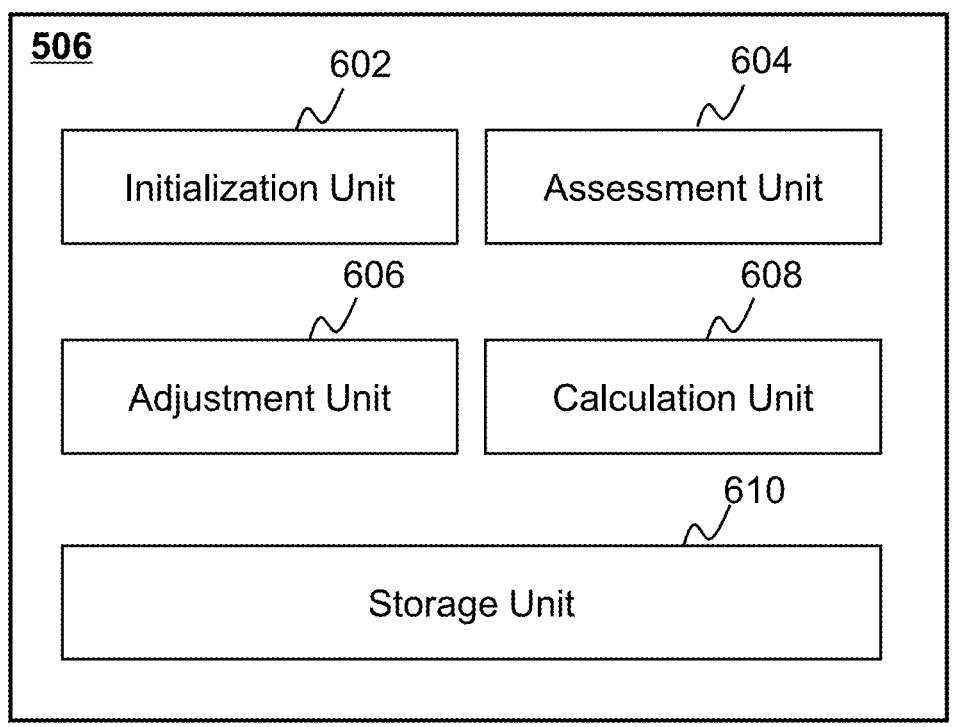
FIG. 6 is a block diagram illustrating an exemplary processing module according to some embodiments of the present disclosure.

FIG. 6 is a block diagram illustrating an exemplary processing module 506 according to some embodiments of the present disclosure. As shown, the processing module 506 may include an initialization unit 602, an assessment unit 604, an adjustment unit 606, a calculation unit 608, and a storage unit 610. The processing module 506 may be implemented on various components (e.g., the processor 310 of the computing device 300 as illustrated in FIG. 3). For example, at least a portion of the processing module 506 may be implemented on a computing device as illustrated in FIG. 3 or a mobile device as illustrated in FIG. 4.

The initialization unit 602 may initialize at least one portion of imaging parameters. For example, the initialization unit 602 may provide an initial flip angle schedule including multiple initial flip angle values. In some embodiments, the initialization unit 602 may initialize an imaging parameter relating to an initial flip angle schedule (e.g., a starting flip angle and an ending flip angle in a phase of an echo train) to determine an initial flip angle schedule. In some embodiments, the initialization unit 602 may transmit an initialization result to other units in the processing module 506 for further processing. For example, the initialization unit 602 may transmit an initial flip angle schedule to the assessment unit 604 for assessing.

The assessment unit 604 may perform an assessment function in a process for determining a target flip angle schedule. For example, the assessment unit 604 may determine whether a flip angle schedule (e.g., an initial flip angle schedule provided by the initialization unit 602) satisfies a criterion, a standard, or a threshold. In some embodiments, the assessment unit 604 may transfer an assessment result to other units in the processing module 506 for further processing. For example, the assessment unit 604 may transfer an assessment result to the adjustment unit 606 for adjusting a flip angle schedule.

The adjustment unit 606 may adjust at least one portion of imaging parameters. For example, the adjustment unit 606 may adjust at least one portion of a flip angle schedule (e.g., an initial flip angle schedule provided by the initialization unit 602 or an intermediate flip angle schedule). In some embodiments, the adjustment unit 606 may transfer an adjusted flip angle schedule to other units in the processing module 506 for further processing. For example, the adjustment unit 606 may transfer an adjusted flip angle schedule to the storage unit 510 for storing.

The calculation unit 608 may calculate different kinds of information received from the initialization unit 602, the assessment unit 604, the adjustment unit 606, and/or other modules or units in the MRI system 100. For example, the calculation unit 608 may calculate flip angles in an initial flip angle schedule using different functions, and/or algorithms based on the initial information or condition preset. The function(s) may include the Bloch equation, the EPG algorithm, a polynomial, a linear function, a trigonometric function, an anti-trigonometric function, an exponential function, a power function, a logarithmic function, or the like, or a combination thereof. Exemplary algorithms may include recursion, a bisection algorithm, an exhaustive search (or brute-force search), a greedy algorithm, a divide and conquer algorithm, a dynamic programming method, an iterative algorithm, a branch-and-bound algorithm, a backtracking algorithm, or the like, or a combination thereof.

The storage unit 610 may store information including, for example, information for determining a target flip angle schedule. The information may include programs, software, algorithms, data, text, number, and some other information. For example, the storage unit 610 may store an initial flip angle schedule determined by the initialization unit 602, an intermediate flip angle schedule and/or a target flip angle schedule generated by the calculation unit 608 and/or adjustment unit 608. In some embodiments, the storage unit 610 may store a criterion, a threshold, or a standard for assessing an initial flip angle schedule and/or an intermediate flip angle schedule. The storage unit 610 may store intermediate results and/or final results in the process of the target flip determination.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the assessment unit 620 and the adjustment unit 640 may be integrated into one single unit. As another example, the calculation unit 608 may be integrated into the initialization unit 602, the assessment unit 604, and/or the adjustment unit 606. However, those variations and modifications do not depart the scope of the present disclosure.

Figure 7:
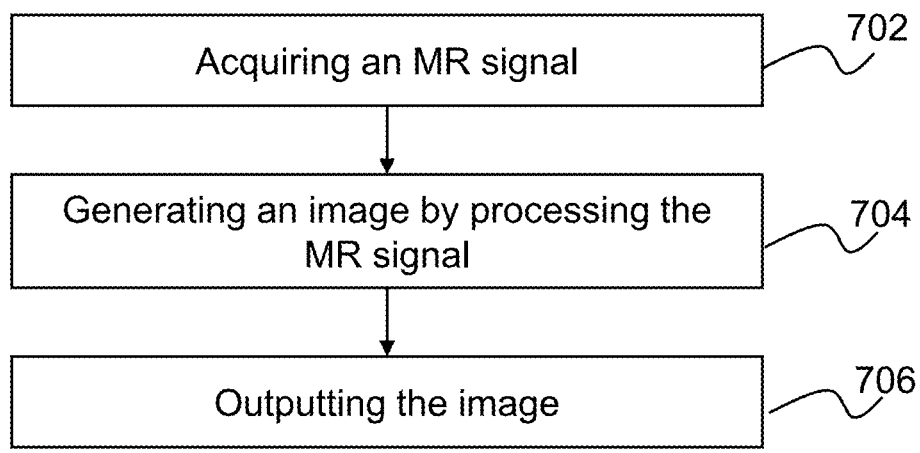
FIG. 7 is a flowchart illustrating an exemplary process for generating an MR image according to some embodiments of the present disclosure.

FIG. 7 is a flowchart illustrating an exemplary process 700 for processing an MR signal according to some embodiments of the present disclosure. In some embodiments, one or more operations of process 700 illustrated in FIG. 7 for processing an MR signal may be implemented in the MRI system 100 illustrated in FIG. 1. For example, the process 700 illustrated in FIG. 7 may be stored in the storage device 130 in the form of instructions, and invoked and/or executed by the processing engine 120 (e.g., the processor 310 of the computing device 300 as illustrated in FIG. 3, the CPU 440 of the mobile device 400 as illustrated in FIG. 4).

In 702, an MR signal may be acquired. Operation 702 may be performed by the acquisition module 502. In some embodiments, the MR signal may be acquired from the MR scanner 110, the storage device 130, the terminal(s) 140, and/or an external data source. For example, the MR signal may be obtained from the MR scanner 110 generated by applying an excitation RF pulse and multiple refocusing RF pulses to a subject being examined. In some embodiments, the multiple refocusing RF pulses may have a target flip angle schedule determined as described in connection with FIGS. 8, 10, 11, and/or 12. In some embodiments, the MR signal may include one or more echo trains with multiple echoes. A type of an echo may include a spin echo, a fast spin echo (FSE), a fast recovery FSE, a single shot FSE, a gradient recalled echo, a fast imaging echo with steady-state precession, etc. In some embodiments, the MR signal may be stored in the storage device 130 and/or the storage module 508 as numerical values. In some embodiments, the MR signal may be expressed as data values in the k-space (also referred to as the frequency domain).

In 704, an image may be generated by processing the MR signal. Operation 704 may be performed by the processing module 506. In some embodiments, the image may be generated by processing the MR signal based on a reconstruction technique. The reconstruction technique may include a Fourier transform (FT), a frequency encoding, a phase encoding, an iterative reconstruction, a backward projection or the like, or a combination thereof. For example, the Fourier transform may include a fast Fourier Transform (FFT), a 2-dimensional FT, a 3-dimensional FT, a Discrete Fourier Transform (DFT), an Inverse Fourier Transform (IFT), an Inverse Fast Fourier Transform (IFFT), or the like, or a combination thereof.

In 706, the image may be outputted. Operation 706 may be performed by the processing module 506. In some embodiments, the image may be outputted to the terminal(s) 140 for display. In some embodiments, the image may be outputted to the storage device 130 and/or the storage module 508 for storing.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, process 700 may include an operation for pre-processing the MR signal before operation 704.

Figure 8:
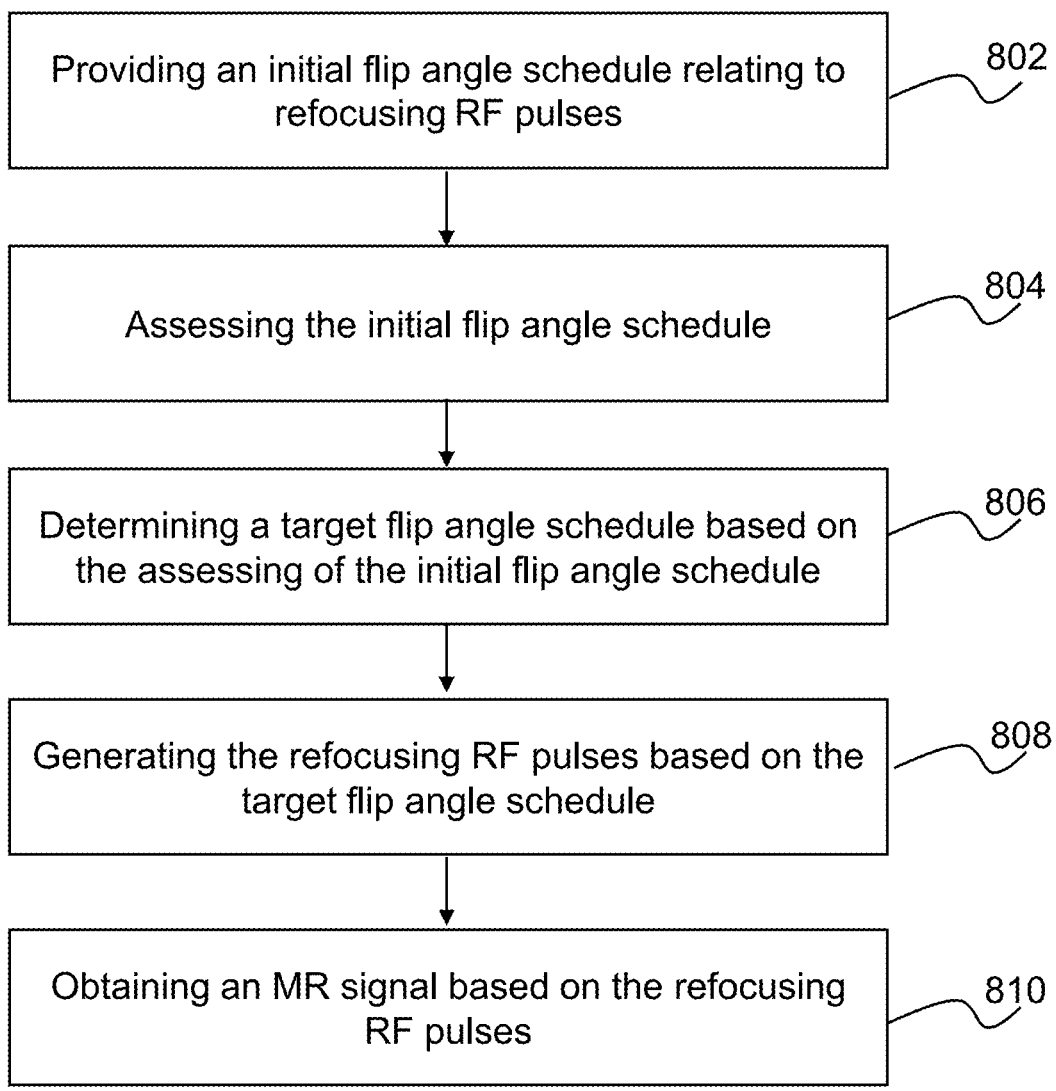
FIG. 8 is a flowchart illustrating an exemplary process for acquiring an MR signal according to some embodiments of the present disclosure.

FIG. 8 is a flowchart illustrating an exemplary process 800 for acquiring an MR signal according to some embodiments of the present disclosure. Operation 702 illustrated in FIG. 7 may be performed according to process 800. In some embodiments, one or more operations of process 800 illustrated in FIG. 8 for processing an MR signal may be implemented in the MRI system 100 illustrated in FIG. 1. For example, the process 800 illustrated in FIG. 8 may be stored in the storage device 130 in the form of instructions, and invoked and/or executed by the processing engine 120 (e.g., the processor 310 of the computing device 300 as illustrated in FIG. 3, the CPU 440 of the mobile device 400 as illustrated in FIG. 4).

In 802, an initial flip angle schedule relating to refocusing RF pulses may be provided. Operation 802 may be performed by the initialization unit 602. In some embodiments, the initial flip angle schedule may include a specific number of initial flip angles with variable initial values or the same initial value. In some embodiments, the initial flip angle schedule may be divided into one or more portions corresponding to one or more phases of an echo train. A used herein, the phases of an echo train may indicate the trend of an echo train. For example, the echo train may be divided into three phases, including a first phase, a second phase, and a third phase. In each phase, the echo signals in the echo train may have a trend different from one or both of the other two phases. For example, the trend of the echo signals in the first phase is substantially a steady state indicating that the echo signals in the first phase do not change significantly. Therefore, the phases may be utilized to indicate the number of groups or phases into which the flip angles of the refocusing RF pulses are divided. For example, the initial flip angle schedule may be divided into three portions corresponding to the first phase, the second phase, and the third phase, respectively. In each phase, the initial flip angles may vary monotonically. For example, one portion of the initial flip angles corresponding to the first phase may be decreasing monotonically, one portion of the initial flip angles corresponding to the second phase may be increasing monotonically, and the last portion of the initial flip angles corresponding to the third phase may be decreasing monotonically.

In some embodiments, the initial flip angle schedule may be determined by determining flip angles in each phase. In some embodiments, some of the imaging parameters for different phases may be different, and some of the imaging parameters for different phases may be the same. For example, the T1 or T2 value for different phases of the echo train for the same tissue of a subject may be the same. In some embodiments, the initial flip angle schedule may be determined using a function and/or an algorithm based on at least one portion of imaging parameters. For example, the function may include the Bloch equation, the EPG algorithm, a polynomial, a linear function, a trigonometric function, an anti-trigonometric function, an exponential function, a power function, a logarithmic function, or the like, or a combination thereof. Exemplary algorithms may include recursion, a bisection algorithm, an exhaustive search (or brute-force search), a greedy algorithm, a divide and conquer algorithm, a dynamic programming technique, an iterative algorithm, a branch-and-bound algorithm, a backtracking algorithm, or the like, or a combination thereof. In some embodiments, the initial flip angle schedule may be set by a user via the terminal(s) 140 or may be a default setting of the MRI system 100. For example, flip angles in the initial flip angle schedule may have suitable values in a range and vary based on a rule, such as in a range from 90° to 180° increasing monotonically.

In 804, the initial flip angle schedule may be assessed. Operation 804 may be performed by the assessment unit 604. In some embodiments, the initial flip angle may be assessed based on a signal evolution corresponding to the initial flip angle schedule. The signal evolution may correspond to an echo train with multiple echoes obtained based on multiple refocusing RF pulses with the initial flip angle schedule. The signal evolution may indicate a trend and/or values of signal intensities of echoes in the echo train corresponding to the initial flip angle schedule. In some embodiments, the assessment may be based on whether one or more echo signals in the signal evolution satisfy a requirement, a criterion, a threshold, or a standard. In some embodiments, the assessment may be based on whether a section (e.g., a phase or a portion) of the signal evolution satisfy a criterion, a threshold, or a standard. In some embodiments, the assessment may be based on a comparison between the signal evolution with a reference signal evolution. Both the signal evolution and the reference signal evolution may correspond to an echo train respectively, and the echo train may be divided into one or more phases. The reference signal evolution may correspond to one or more echo trains with an expected signal intensity of each echo. Alternatively, the reference signal evolution may be a restriction on the signal intensity of one or more echoes, e.g., the signal intensity of the starting echo, the signal intensity of the ending echo of each phase of an echo train, the signal intensity of an nth echo in the echo train, or the like, or a combination thereof. As a further example, the reference signal evolution may specify a desired signal intensity, without specifying how or when the corresponding echo (the echo that corresponds to the signal of the specified intensity) occurs in the echo train. In some embodiments, the reference signal evolution may include a restriction on the trend of each phase in one or more echo trains. The trend may be increasing, decreasing, steady state, plateau, or the like. It should be noted that the trend restriction may be applied to any number of phases in the echo train.

In some embodiments, the signal evolution may be determined based on a relationship between flip angles and echo signals. For example, the relationship may be described by, e.g., the Bloch equation, the EPG algorithm, or the like, or a combination thereof. In some embodiments, the signal evolution may be determined in accordance of T1 and T2 of a tissue of a subject being examined. Alternatively, the calculation of the signal evolution may also be performed regardless of the relaxation time of a tissue. In some embodiments, the reference signal evolution may be selected or defined by a user. In some embodiments, the reference signal evolution may be selected by the MRI system 100 based on information provided by a user. Exemplary information may include an actual imaging to be performed, the subject to be imaged, T1 of the subject, T2 of the subject, the proton density of a desired subject, or the like, or a combination thereof. More descriptions of the signal evolution may be found in, for example, International Patent Application No. PCT/CN2015/087818 entitled "SYSTEM AND METHOD FOR FLIP ANGLE DETERMINATION IN MAGNETIC RESONANCE IMAGING," filed Aug. 21, 2015, the contents of which are hereby incorporated by reference.

In some embodiments, the initial flip angle schedule may be assessed based on one or more criteria. For example, the assessment of the initial flip angle schedule may include determining whether the initial flip angle schedule satisfies a first criterion and/or a second criterion. If the initial flip angle schedule satisfies the first criterion, the initial flip angle schedule may be assessed according to the second criterion. If the initial flip angle schedule does not satisfy the first criterion, the initial flip angle schedule may be adjusted to obtain an intermediate flip angle schedule that satisfies the first criterion. Then the intermediate flip angle schedule may be assessed according to the second criterion. In some embodiments, the assessment of the initial flip angle may include determining and/or assessing one or more intermediate flip angle schedules based on the first criterion and/or the second criterion.

In 806, a target flip angle schedule may be determined based on the assessment of the initial flip angle schedule. Operation 806 may be performed by the adjustment unit 606. In some embodiments, the target flip angle schedule may be determined by adjusting the initial flip angle schedule repeatedly according to one or more criteria (e.g., the first criterion and the second criterion). For example, the initial flip angle schedule may be adjusted to obtain an intermediate flip angle schedule (e.g., the first flip angle schedule) if the initial flip angle schedule does not satisfy the first criterion. The intermediate flip angle schedule may be adjusted to obtain another intermediate flip angle schedule (e.g., the second flip angle schedule) if the intermediate flip angle schedule does not satisfy the second criterion. In some embodiments, multiple intermediate flip angle schedules may be generated and adjusted to obtain the target flip angle schedule that satisfies the first criterion and the second criterion simultaneously.

In 808, the refocusing RF signals may be generated based on the target flip angle schedule. Operation 808 may be performed by control module 504. In some embodiments, one or more parameters relating to the refocusing RF signals may be determined based on the target flip angle schedule. The parameters relating to the refocusing RF signals may include an intensity of a refocusing RF pulse, a refocusing interval (i.e., an interval time between two refocusing RF pulse), the number of the refocusing RF pulses, etc. For example, an intensity of a refocusing RF pulse may be greater if the value of the flip angle of the refocusing RF pulse is larger. In some embodiments, the control module 504 may direct the RF coil 240 to generate the refocusing RF signals based on the parameters relating to the refocusing RF pulses determined based on the target flip angle schedule.

In 810, an MR signal may be obtained based on the refocusing RF pulses.

Operation 810 may be performed by the acquisition module 502. In some embodiments, the MR signal may be obtained from the MR scanner 110 generated by scanning a subject being examined via the refocusing RF pulses with the target flip angle schedule. In some embodiments, the MR signal may be obtained from the storage device 130, the storage module 508 and/or other external storages. In some embodiments, the MR signal may include a spin echo, a fast spin echo (FSE), a fast recovery FSE, a single shot FSE, a gradient recalled echo, a fast imaging with steady-state precession as described elsewhere in the disclosure. In some embodiments, the MR signal may include an echo train with multiple echoes. An echo may correspond to a refocusing RF pulse with a target flip angle. In some embodiments, a parameter relating to the MR signal may be determined based on the target flip angle schedule and/or a parameter relating to the refocusing RF pulses. For example, an echo intensity may be determined based on a target flip angle of a refocusing RF pulse. As another example, an echo time may be determined based on a refocusing interval of two refocusing RF pulses.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 802 and 804 may be performed simultaneously. In some embodiments, the number and length of the phase(s) may be variable, changeable, or adjustable based on the spirits of the present disclosure. For example, the number of phases in an echo train may be one, two, three, or more, or equal to the number of echoes.

Figure 9:
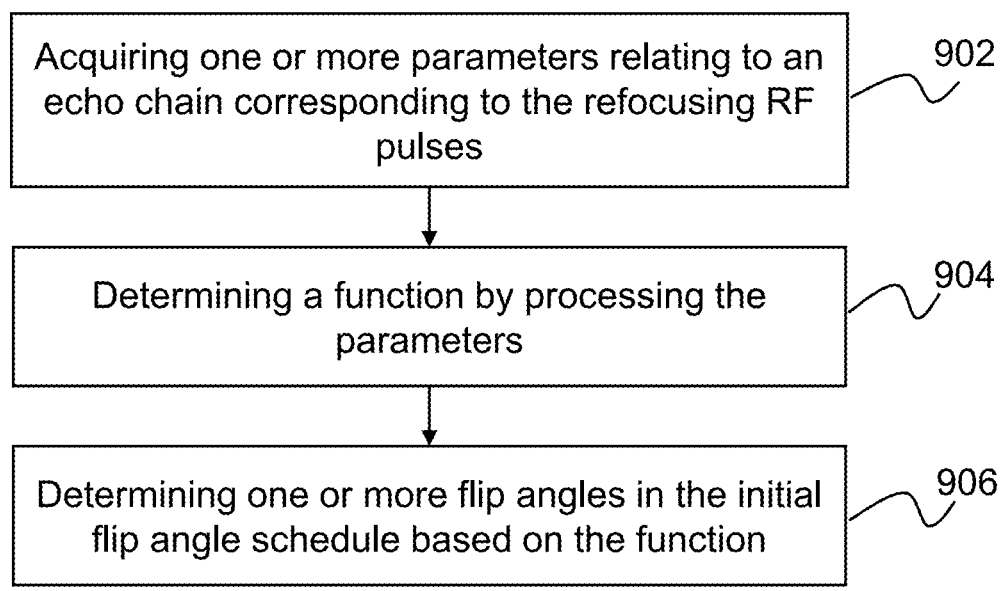
FIG. 9 is a flowchart illustrating an exemplary process for providing an initial flip angle schedule according to some embodiments of the present disclosure.

FIG. 9 is a flowchart illustrating an exemplary process 900 for providing an initial flip angle schedule according to some embodiments of the present disclosure. Operation 802 as described in FIG. 8 may be performed according to process 900. In some embodiments, one or more operations of process 900 illustrated in FIG. 9 for processing an MR signal may be implemented in the MRI system 100 illustrated in FIG. 1. For example, the process 900 illustrated in FIG. 9 may be stored in the storage device 130 in the form of instructions, and invoked and/or executed by the processing engine 120 (e.g., the processor 310 of the computing device 300 as illustrated in FIG. 3, the CPU 440 of the mobile device 400 as illustrated in FIG. 4).

In 902, one or more parameters relating to an echo train corresponding to the refocusing RF signals may be acquired. Operation 902 may be performed by the initialization unit 602. The parameters relating to the echo train may include at least one portion of imaging parameters as described elsewhere in the disclosure. For example, the imaging parameters may include image contrast and/or ratio, a subject of interest, slice thickness, an imaging type (e.g., a T1 weighted imaging, a T2 weighted imaging, a proton density weighted imaging, etc.), T1, T2, a spin echo type (e.g., a spin echo, a fast spin echo (FSE), a fast recovery FSE, a single shot FSE, a gradient recalled echo, a fast imaging with steady-state precession, etc.), a flip angle value, an acquisition time (TA), an echo time (TE), a repetition time (TR), an echo train length (ETL), the number of phases, the number of excitations (NEX), an inversion time, a bandwidth (e.g., RF receiver bandwidth, RF transmitter bandwidth, etc.), or the like, or a combination thereof.

In some embodiments, an initial condition may be determined. The initial condition may include an initial value corresponding to the one or more parameters relating to the echo train corresponding to the refocusing RF pulses. In some embodiments, the initial condition may include a range of the starting flip angle and/or the ending flip angle, and the magnitude of the starting flip angle and the ending flip angle may be limited to the range. As used herein, a starting flip angle for a phase of a flip angle schedule may refer to the flip angle corresponding to the starting point of a phase of MR signals (e.g., a reference signal evolution, an echo train); an ending flip angle for the same phase of a flip angle schedule may refer to the flip angle corresponding to the ending point of the phase of MR signals (e.g., a reference signal evolution, an echo train, etc.). In some embodiments, the initial condition (e.g., values of the starting flip angle and/or the ending flip angle) may be determined by a user via the terminal(s) 140. In some embodiments, the initial condition (e.g., a range for the starting flip angle and/or the ending flip angle) may be determined by the processing engine 120 based on clinical demands. For example, in a cervical spine imaging or a knee joint imaging, the maximum flip angle of an echo train may be set to be lower than 120°. As another example, in an abdominal imaging, the minimum flip angle may be greater than 80°. As still another example, in a hip joint imaging, a maximum flip angle may be set to be 140°. In some embodiments, in each phase, the starting flip angle may be the maximum flip angle, and the ending flip angle may be the minimum flip angle in the phase.

In 904, a function may be determined by processing the parameters.

Operation 902 may be performed by the initialization unit 602. The function may be used to describe an initial flip angle schedule or a portion thereof (e.g., a phase of the entire initial flip angle schedule). In some embodiments, the function may include a Bloch equation, an EPG algorithm, a polynomial function, a linear function, a trigonometric function, an anti-trigonometric function, an exponential function, a power function, a logarithmic function, or the like, or a combination thereof. In some embodiments, the function corresponding to the initial flip angle schedule may be determined based on one or more parameters, for example, a starting flip angle, an ending flip angle and/or a characteristic parameter. As used herein, the characteristic parameter may control or affect the rate of the flip angles change. For example, an echo train may be divided into one or more phases. In a phase, the flip angles of the refocusing RF pulses may vary in accordance with, e.g., an exponential function. For example, assuming that N is the echo train length (ETL), $\alpha_0$ is the starting flip angle of a phase, $\alpha_{N-1}$ is the ending flip angle of that phase, the flip angles in one phase may be described using the following functions: if $\alpha_{N-1} \geq \alpha_0$, the remaining flip angles of the phase may be calculated by Equation (1) as illustrated as below:

$$\alpha_n = \alpha_n + (\alpha_{N-1} - \alpha_0) \cdot \frac{e^{\left(\frac{n^2}{P^2}\right)} - 1}{e^{\left(\frac{(N-1)^2}{P^2}\right)} - 1}, ; \tag{1}$$

If $\alpha_0 > \alpha_{N-1}$, the remaining flip angles of the phase may be calculated by Equation (2) as illustrated below:

$$\alpha_n = \alpha_{N-1} + (\alpha_0 - \alpha_{N-1}) \cdot \frac{e^{\left(\frac{(N-1-n)^2}{P^2}\right)} - 1}{e^{\left(\frac{(N-1)^2}{P^2}\right)} - 1}, \tag{2}$$

where n=0, 1, . . . , N−1, P is a characteristic parameter. In some embodiments, P may control or affect the rate of the flip angles change around the starting point and the ending point in a phase. P may be a real number that is greater than 1. P of one phase may be different from that of another phase.

In some embodiments, the echo train may be divided into one or more phases. In a phase, the flip angles of the refocusing RF pulses may vary in accordance with, e.g., a linear function. For example, assuming that N is the echo train length (ETL), $\alpha_0$ is the starting flip angle of a phase, $\alpha_{N-1}$ is the ending flip angle of that phase, the flip angles in one phase may be described using Equation (3) as illustrated below:

$$\alpha_n = \frac{n}{N-1}(\alpha_{N-1} - \alpha_0) + \alpha_0, \tag{3}$$

where n=0, 1, . . . , N−1.

In some embodiments of the present disclosure, the echo train may be divided into one or more phases. In each phase, the flip angles of the refocusing RF pulses may vary in accordance with, e.g., a polynomial. Merely by way of example, assuming that N is the echo train length (ETL), $\alpha_0$ is the starting flip angle of a phase, $\alpha_{N-1}$ is the ending flip angle of that phase, the flip angles in one phase may be described using Equation (4) as illustrated below:

$$\alpha_n = \alpha_0 + \Sigma_{l=1}^{K} P_l \cdot n^l, \tag{4}$$

where n=0, 1, . . . , N−1. P=[$P_1$, $P_2$, . . . , $P_K$] is a vector of characteristic parameters. In some embodiments, K may be an integer less than 10. $P_1, P_2, \ldots, P_K$ may be selected so that the flip angle schedule may be either monotonically increasing or monotonically decreasing, and meet the criteria that:

$$\alpha_{N-1}=\alpha_0+\Sigma_{I=1}^{K} P_I (N-1)^I, \qquad (5).$$

In 906, one or more flip angles in the initial angle schedule may be determined based on the function (e.g., Equation (1), Equation (2), Equation (3), Equation (4), and/or Equation (5)). Operation 902 may be performed by the initialization unit 602. In some embodiments, the remaining flip angles in the initial flip angle schedule may be determined according to the function (e.g., Equation (1), Equation (2), Equation (3), Equation (4), and/or Equation (5)). More descriptions of determining the initial flip angle schedule corresponding to multiple phases may be found in, for example, International Patent Application No. PCT/CN2015/087818 entitled "SYSTEM AND METHOD FOR FLIP ANGLE DETERMINATION IN MAGNETIC RESONANCE IMAGING," filed Aug. 21, 2015, the contents of which are hereby incorporated by reference.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 904 may be unnecessary. In some embodiments, the function determined in 904 may be described by other equations.

Figure 10:
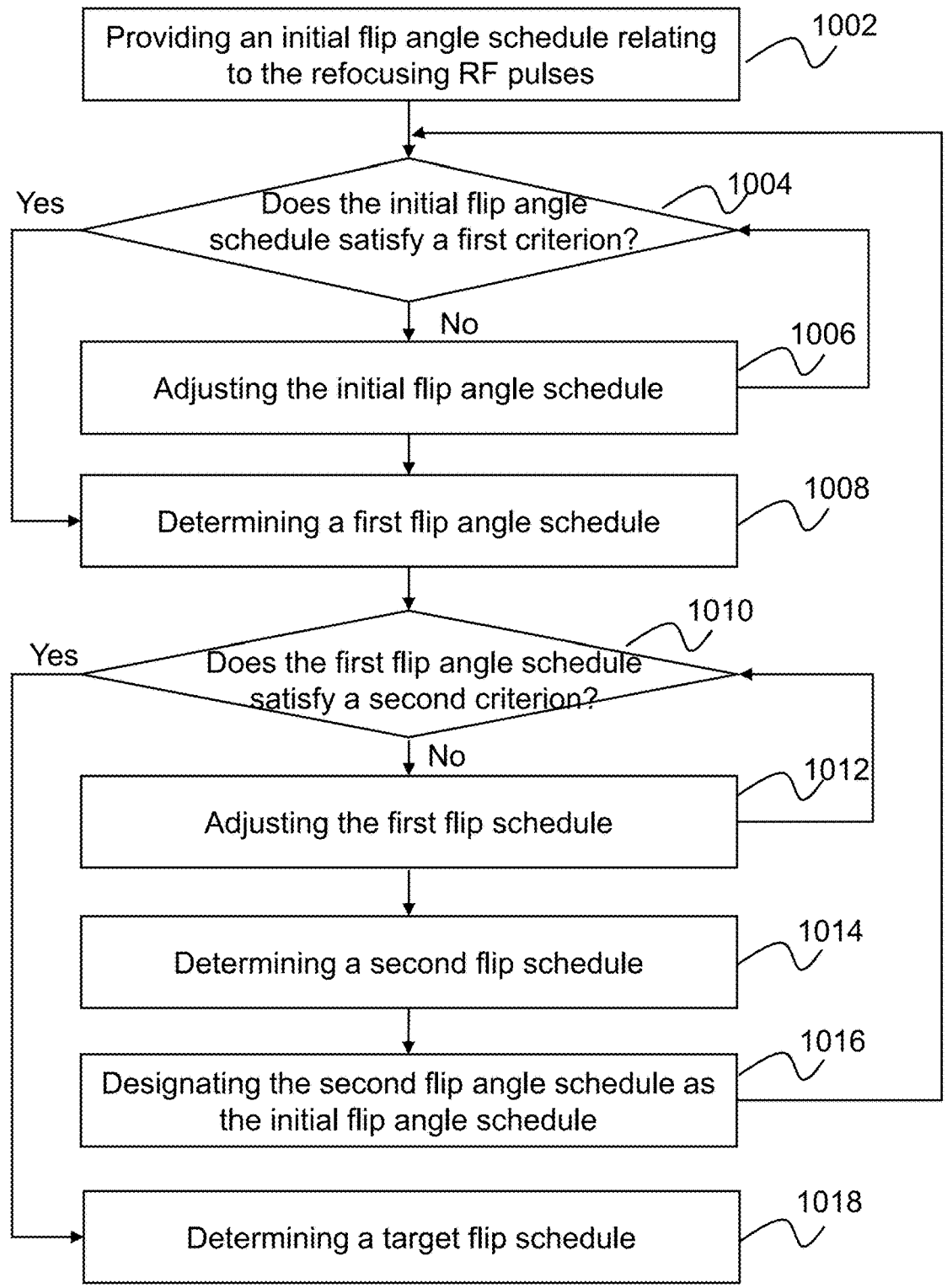
FIG. 10 is a flowchart illustrating an exemplary process for determining a target flip angle schedule according to some embodiments of the present disclosure.

FIG. 10 is a flowchart illustrating an exemplary process 1000 for determining a target flip angle schedule according to some embodiments of the present disclosure. In some embodiments, the target flip angle schedule may be determined based on an initial flip angle schedule and one or more criteria relating to one or more parameters relating to an echo train or multiple refocusing RF pulses (e.g., a signal intensity of an echo, a total energy of multiple refocusing RF pulses, etc.). For example, the target flip angle schedule may be determined based on a total energy of multiple refocusing RF pulses. A flip angle of a refocusing RF pulse may relate to an energy of the refocusing RF pluses. A greater flip angle may correspond to a greater energy. The total energy of multiple refocusing RF pulses may relate to a specific absorption rate (SAR) of a subject (e.g., tissue). The greater the total energy of multiple refocusing RF pulses may be, the greater the SAR may be. Thus, the total energy of the multiple refocusing RF pulses may be adjusted by adjusting flip angles in the initial flip angle schedule to reduce the SAR. Operation 804 illustrated in FIG. 8 may be performed according to process 1000. In some embodiments, one or more operations of process 1000 illustrated in FIG. 10 for processing an MR signal may be implemented in the MRI system 100 illustrated in FIG. 1. For example, the process 1000 illustrated in FIG. 10 may be stored in the storage device 130 in the form of instructions, and invoked and/or executed by the processing engine 120 (e.g., the processor 310 of the computing device 300 as illustrated in FIG. 3, the CPU 440 of the mobile device 400 as illustrated in FIG. 4).

In 1002, an initial flip angle schedule relating to the refocusing RF signals may be provided. Operation 1002 may be performed by the initialization unit 602. In some embodiments, the initial flip angle schedule may be determined as described in connection with FIGS. 8 and 9.

In 1004, a determination may be made as to whether the initial flip angle schedule satisfies a first criterion. Operation 1004 may be performed by the assessment unit 604. If the initial flip angle schedule satisfies the first criterion, process 1000 may proceed to operation 1008. If the initial flip angle schedule does not satisfy the first criterion, process 1000 may proceed to operation 1006. In some embodiments, the first criterion may include a first threshold. The first threshold may relate to a first parameter relating to an echo train obtained based on the refocusing RF signals with the initial flip angle schedule. For example, the first parameter relating to the echo train may include a signal intensity of an echo in the echo train. In some embodiments, the initial flip angle schedule does not satisfy the first criterion if the first parameter is lower than the first threshold. The initial flip satisfies the first criterion if the first parameter is equal to or exceeds the first threshold. In some embodiments, the initial flip angle schedule does not satisfy the first criterion if a difference between the first parameter and the first threshold is greater than a fourth threshold (e.g., a constant). The initial flip angle schedule satisfies the first criterion if the difference between the first parameter and the first threshold is lower than or equal to a fourth threshold (e.g., a constant).

In some embodiments, the first criterion may further include a second threshold, in addition to the first threshold. The second threshold may relate to a second parameter relating to the refocusing RF signals with the initial flip angle schedule. For example, the second parameter may include a total energy of the refocusing RF signals with the initial flip angle schedule. In some embodiments, the initial flip angle schedule does not satisfy the first criterion if the second parameter exceeds the second threshold. The initial flip angle schedule satisfies the first criterion if the second parameter is lower than or equal to the second threshold. In some embodiments, the initial flip angle schedule does not satisfy the first criterion if a difference between the second parameter and the second threshold is lower than a fifth threshold (e.g., a constant). The initial flip angle schedule satisfies the first criterion if the difference between the second parameter and the second threshold is equal to or exceeds a fifth threshold (e.g., a constant). In some embodiments, the initial flip angle schedule does not satisfy the first criterion if the first parameter does not satisfy the first threshold and the second parameter does not satisfy the second threshold simultaneously. In some embodiments, the first threshold and the second threshold may be set by a user according to clinical demands (e.g., the type of tissue being examined). In some embodiments, the first threshold and the second threshold may be determined by the processing engine 120 according to, for example, a reference signal evolution as described in connection with FIG. 8 and/or FIG. 11. As used herein, the fourth threshold and the fifth threshold may be relatively small values (e.g., values in a range from 0 to 1). In some embodiments, the fourth threshold and the fifth threshold may be set by a user or according to a default setting of the MRI system 100.

In some embodiments, the determination that whether the initial flip angle schedule satisfies the first criterion may be made based on a first signal evolution corresponding to the initial flip angle schedule. The first signal evolution may include an echo train with multiple echoes obtained based on multiple refocusing RF pulses with the initial flip angle schedule. In some embodiments, the determination that whether the initial flip angle schedule satisfies the first criterion may be made based on whether one or more echo signals in the signal evolution does not satisfy the first criterion.

In 1006, the initial flip angle schedule may be adjusted. Operation 1006 may be performed by the adjustment unit

606. In some embodiments, one or more flip angles in the initial flip angle schedule may be adjusted (e.g., increased or decreased) to obtain the first flip angle schedule. In some embodiments, the initial flip angle schedule may be adjusted by adjusting one or more parameters relating to the echo train corresponding to the initial angle schedule (e.g., the starting flip angle, the ending flip angle, the characteristic parameter) using an algorithm. Exemplary algorithms may include a bisection algorithm, an exhaustive search (or brute-force search) algorithm, a greedy algorithm, a divide and conquer algorithm, a dynamic programming algorithm, an iterative algorithm, a branch-and-bound algorithm, a backtracking algorithm, or the like, or a combination thereof. In some embodiments, the adjusted initial flip angle schedule may be assessed based on the first criterion as illustrated in 1004.

In 1008, the first flip angle schedule may be determined. Operation 1008 may be performed by the assessment unit 604. The first flip angle schedule may satisfy the first criterion. For example, the first parameter relating to the echo train obtained based on multiple refocusing RF pulses with the first flip angle schedule may satisfy the first threshold and the second parameter relating to the multiple refocusing RF pulses with the first flip angle schedule may satisfy the second threshold. In some embodiments, the initial flip angle schedule may be designated as the first flip angle schedule if the initial flip angle schedule satisfies the first criterion.

In 1010, a determination may be made as to whether the first flip angle schedule satisfies a second criterion. Operation 1010 may be performed by the assessment unit 604. If the first flip angle schedule satisfies the second criterion, process 1000 may proceed to operation 1018. If the first flip angle schedule satisfies the second criterion, process 1000 may proceed to operation 1012. In some embodiments, the second criterion may include a third threshold. The third threshold may relate to a third parameter relating to an echo train. In some embodiments, the third parameter relating to an echo train may include an equivalent TE of the first echo train generated based on the refocusing RF pulses with the first flip angle schedule. In some embodiments, the first flip angle schedule does not satisfy the second criterion if the equivalent TE of the first echo train is lower than the third threshold. The first flip angle schedule satisfies the second criterion if the equivalent TE of the first echo train equals to or exceeds the third threshold. In some embodiments, the first flip angle schedule does not satisfy the second criterion if a difference between the equivalent TE of the first echo train and the third threshold exceeds a sixth threshold (e.g., a constant). The first flip angle schedule satisfies the second criterion if the difference between the equivalent TE of the first echo train and the third threshold is lower than or equal to a sixth threshold (e.g., a constant). In some embodiments, the third threshold may be determined according to, for example, a reference signal evolution as described in connection with FIG. 8 and/or FIG. 11. As used herein, the sixth threshold may be a relatively small value (e.g., a constant in the range from 0 to 1). In some embodiments, the sixth threshold may be set by a user or according to a default setting of the MRI system 100.

In some embodiments, the determination that the first flip angle schedule does not satisfy the second criterion may be based on a second signal evolution corresponding to the first flip angle schedule. The second signal evolution may include an echo train with multiple echoes obtained based on multiple refocusing RF pulses with the first flip angle schedule. In some embodiments, the determination that the first flip angle schedule does not satisfy the second criterion may be based on whether the center echo in the second signal evolution does not satisfy the second criterion.

In 1012, a first flip angle schedule may be adjusted. Operation 1012 may be performed by the adjustment unit 606. In some embodiments, a certain number of flip angles in the first flip angle schedule may be increased or decreased to obtain the second flip angle schedule. The certain number of flip angles in the first flip angle schedule needed to be adjusted may be determined based on the second criterion as described in connection with FIG. 12. In some embodiments, the first flip angle schedule may be adjusted by adjusting one or more parameters relating to the echo train corresponding to the first angle schedule (e.g., a starting flip angle, an ending flip angle, a characteristic parameter) using an algorithm. Exemplary algorithms may include recursion, a bisection method, an exhaustive search (or brute-force search), a greedy algorithm, a divide and conquer algorithm, a dynamic programming technique, an iterative algorithm, a branch-and-bound algorithm, a backtracking algorithm, or the like, or a combination thereof. In some embodiments, the adjusted first flip angle schedule may be assessed based on the second criterion as illustrated in 1010.

In 1014, a second flip angle schedule may be determined. Operation 1014 may be performed by the assessment unit 604. The second flip angle schedule may satisfy the second criterion. For example, the equivalent TE of an echo train obtained based on multiple refocusing RF pulses with the second flip angle schedule may satisfy the third threshold (e.g., a desired equivalent TE).

In 1016, the second flip angle schedule may be designated as the initial flip angle schedule. Operation 101 may be performed by the initialization unit 602. In some embodiments, the second flip angle schedule may be assessed based on the first criterion and/or the second criterion described in connection with operations 1004-1018.

In 1018, a target flip angle schedule may be determined. Operation 1018 may be performed by the adjustment unit 606. In some embodiments, operations 1004 to 1016 may be performed repeatedly unit the target flip angle schedule is determined. The target flip angle schedule may satisfy the first criterion and the second criterion simultaneously. In some embodiments, the first flip angel schedule determined in 1008 may be determined as the target flip angle schedule.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 1002 may be unnecessary. As another example, operations 1006 and 1008 may be performed simultaneously.

Figure 11:
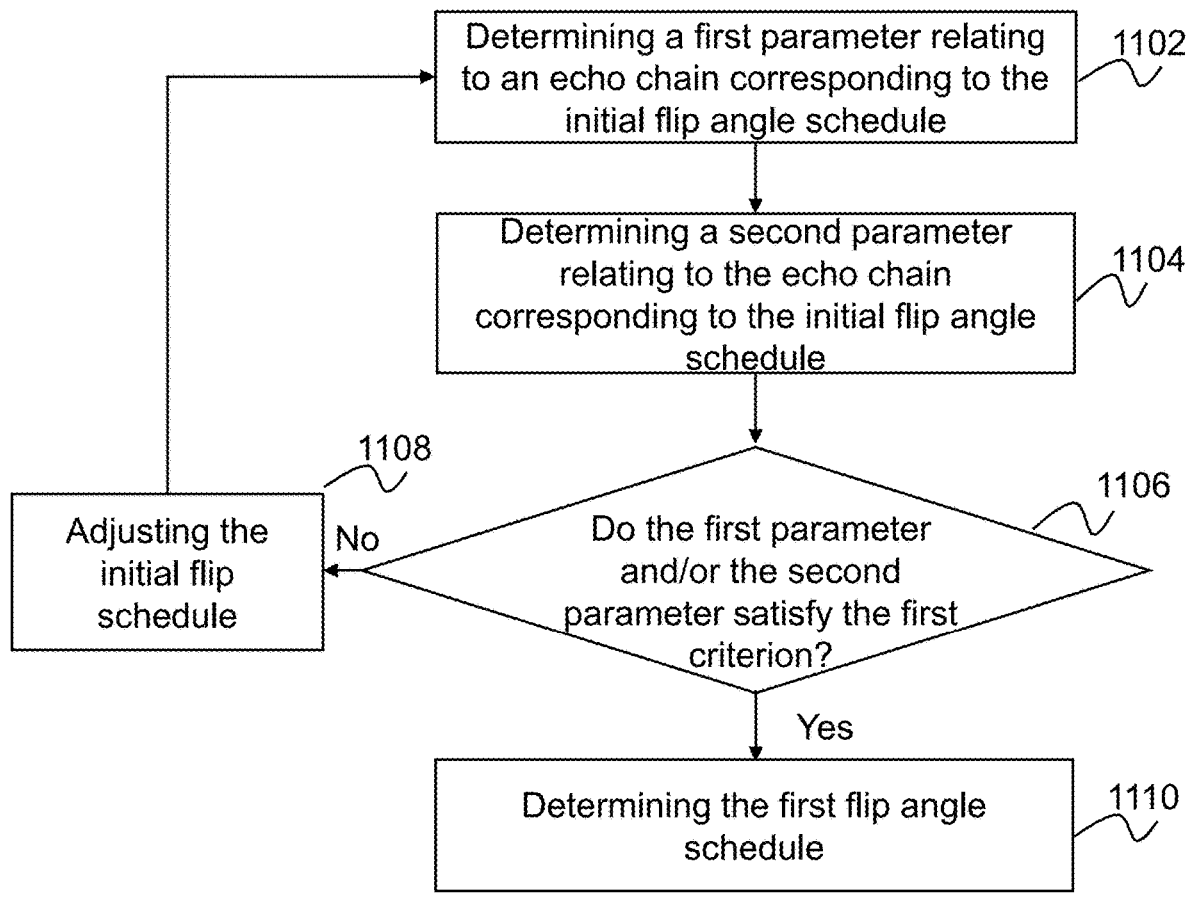
FIG. 11 is a flowchart illustrating an exemplary process for assessing an initial flip angle schedule according to some embodiments of the present disclosure.

FIG. 11 is a flowchart illustrating an exemplary process 1100 for assessing an initial flip angle schedule according to some embodiments of the present disclosure. In some embodiments, one or more operations of process 1100 illustrated in FIG. 11 for processing an MR signal may be implemented in the MRI system 100 illustrated in FIG. 1. For example, the process 1100 illustrated in FIG. 11 may be stored in the storage device 130 in the form of instructions, and invoked and/or executed by the processing engine 120 (e.g., the processor 310 of the computing device 300 as illustrated in FIG. 3, the CPU 440 of the mobile device 400 as illustrated in FIG. 4). Operation 1004 as described in FIG. 10 may be performed according to process 1100.

In 1102, a first parameter relating to an echo train corresponding to an initial flip angle schedule may be determined. Operation 1102 may be performed by the calculation unit 608. In some embodiments, the initial flip angle schedule may be determined as described in connection with FIGS. 8, 9, and/or 10. The echo train may be obtained based on multiple refocusing RF pulses with the initial flip angle schedule. In some embodiments, the multiple RF pulses with the initial flip angle schedule may be defined by other parameters, such as a refocusing interval between two adjacent refocusing RF pulses, a serial number of a refocusing RF pulse, the total energy of the multiple refocusing RF pulses, etc.

In some embodiments, the first parameter may relate to a signal intensity of an echo in the echo train corresponding to the initial flip angle schedule. In some embodiments, the signal intensity of an echo in the echo train may be determined based on a relationship between an echo and a flip angle of a refocusing RF pulse. For example, the relationship may be described by, the Bloch equation, the EPG algorithm, or the like, or a combination thereof. In some embodiments, the signal intensity of an echo may be determined based on a longitudinal relaxation time T1 and a transverse relaxation time T2 of a tissue being examined. For example, a signal intensity of an echo in the echo train may be determined based on Equation (6) as illustrated below:

$$S(TE)=S_0 * f_\alpha * f_t(TE,T1,T2), \quad (6)$$

where S(TE) denotes the signal intensity of an echo, $S_0$ denotes a constant, TE denotes an echo time, T1 denotes a longitudinal relaxation time of a tissue, T2 denotes a transverse relaxation time of the tissue, and $f_\alpha$ denotes a signal intensity factor. The signal intensity factor $f_\alpha$ may relate to the flip angle of a refocusing RF pulse. For example, the greater the flip angle is, the greater the signal intensity factor $f_\alpha$ may be. Furthermore, the signal intensity factor $f_\alpha$ may be less than 1 if the flip angle of a refocusing RF pulse is less than 180°.

In some embodiments, the first parameter may include a specific signal intensity. For example, the specific signal intensity may be a maximum signal intensity. The maximum signal intensity may be determined based on a first signal evolution corresponding to the initial flip angle schedule. The first signal evolution may include signal intensities of all echoes in the echo train obtained based on the multiple refocusing RF pulses with the initial flip angle schedule. In some embodiments, the first signal evolution may be determined based on, for example, Equation (6). As another example, the specific signal intensity may be the signal intensity of a center echo of the echo train. In some embodiments, the center echo of the echo train may be determined based on an initial equivalent TE (also referred to as an echo time of the center echo) of the echo train corresponding to the initial flip angle schedule. The initial equivalent TE may be determined by a user via the terminal(s) 140 or may be determined according to a default setting of the MRI system 100. A center refocusing RF pulse corresponding to the center echo may be determined based on the initial equivalent TE. The signal intensity factor $f_\alpha$ of the center refocusing RF pulse may be determined based on the flip angle of the center refocusing RF pulse in the initial flip angle schedule. Then the signal intensity of the center echo may be determined according to Equation (6) based on the determined signal intensity factor $f_\alpha$ of the center refocusing RF pulse and the initial equivalent TE. As still another example, the specific signal intensity may be the signal intensity of an echo corresponding to a refocusing RF pulse with a maximum flip angle in the initial flip angle schedule. Then the specific signal intensity may be determined according to Equation (6) as described above.

In 1104, a second parameter relating to the echo train may be determined. Operation 1104 may be performed by the calculation unit 608. In some embodiments, the second parameter relating to the echo train may be the total energy of the multiple refocusing pulses with the initial flip angle schedule. In some embodiments, the total energy of the multiple refocusing pulses with the initial angle schedule may be determined based on one or more parameters relating to the multiple refocusing pulses as described elsewhere in the disclosure, such as the total number of the multiple refocusing RF pulses, flip angles of the multiple refocusing RF pulses, a frequency of a refocusing RF pulse, etc. For example, a refocusing RF pulse with a greater flip angle may have a greater energy. As another example, the greater the total number of the multiple refocusing pulses is, the greater the total energy of the multiple refocusing pulses may be.

In 1106, a determination may be made as to whether the first parameter and/or the second parameter satisfy the first criterion. Operation 1106 may be performed by the assessment unit 604. If the first parameter and the second parameter satisfy the first criterion, process 1100 may proceed to operation 1110. If the first parameter and/or the second parameter do not satisfy the first criterion, process 1100 may proceed to operation 1108. In some embodiments, the first criterion may include a first threshold corresponding to the first parameter and/or a second threshold corresponding to the second parameter. Whether the first parameter and/or the second parameter satisfy the first criterion may include whether the first parameter satisfies the first threshold and/or the second parameter satisfies the second threshold. In some embodiments, the first threshold and the second threshold may be set according to a default setting of the MRI system 100 or set by a user via the terminal(s) 140. In some embodiments, the first threshold may be determined based on a reference signal evolution (e.g., an expected signal evolution). In some embodiments, the reference signal evolution may be generated based on multiple refocusing RF pulses with a fixed flip angle schedule. The multiple refocusing RF pulses with the fixed flip angle schedule may have the same flip angle equal to, for example, a maximum flip angle in the initial flip angle schedule. The reference signal evolution may include expected signal intensities. In some embodiments, the first threshold may be a maximum signal intensity in the reference signal evolution. In some embodiments, the first threshold may be a signal intensity of a center echo train generated based on the multiple refocusing RF pulses with the fixed flip angle schedule.

In some embodiments, the first criterion may be satisfied if the first parameter is equal to or exceeds the first threshold and/or the second parameter is less than the second threshold. For example, the first criterion may be satisfied if the signal intensity of center echo of the echo train corresponding to the initial flip angle schedule is equal to or exceeds the signal intensity of the center echo of the echo train corresponding to the fixed flip angle schedule and/or the total energy of the refocusing RF pulses with the initial flip angle schedule is less than the second threshold. In some embodiments, the first criterion may be satisfied if a difference between the first parameter and the first threshold is less than a fourth threshold (e.g., a constant) and/or a difference between the second parameter and the second threshold may be less than a fifth threshold (e.g., a constant). The fourth threshold and the fifth threshold may be set according to a default setting of the MRI system 100 or may be set by a user via the terminal(s) 140. For example, the first criterion may be that the signal intensity of the center echo of the echo train corresponding to the initial flip angle schedule is close to the signal intensity of the center echo of the echo train corresponding to the fixed flip angle schedule and/or the total energy of the multiple refocusing RF pulses with the initial flip angle schedule is close to the second threshold (e.g., a desired value). As used herein, a first value being "close to" a second value may indicate that the deviation between the first value and the second value is less than 40%, or 30%, or 20%, or 15%, or 10%, or 8%, or 5%, or 3%, etc. As another example, the first criterion may be that the maximum signal intensity in the first signal evolution is close to the signal intensity of the center echo of the echo train corresponding to the fixed flip angle schedule and/or the total energy of the multiple refocusing RF pulses with the initial flip angle schedule is close to the second threshold (e.g., a desired value).

In 1108, the initial flip angle schedule may be adjusted. Operation 1108 may be performed by the adjustment unit 606. In some embodiments, at least one portion of the initial flip angle schedule may be adjusted. For example, a flip angle in the initial flip angle schedule corresponding to the center echo may be increased or decreased, such that the signal intensity of the center echo of the echo train corresponding to the initial flip angle schedule may be close or equal to, or exceed the signal intensity of the center echo of the echo train corresponding to the fixed flip angle schedule and/or the total energy of the refocusing RF pulses with the initial flip angle schedule may be less than the second threshold.

In 1110, a first flip angle schedule may be determined. Operation 1110 may be performed by the adjustment unit 608. The first flip angle schedule may satisfy the first criterion. In some embodiments, the adjusted initial flip angle schedule determined in 1110 may be designated as the first flip angle schedule. In some embodiments, the initial flip angle schedule may be designated as the first flip angle schedule if the initial flip angle schedule satisfies the first criterion.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 1108 and 1110 may be performed simultaneously. As another example, operations 1102 and 1104 may be performed simultaneously.

Figure 12:
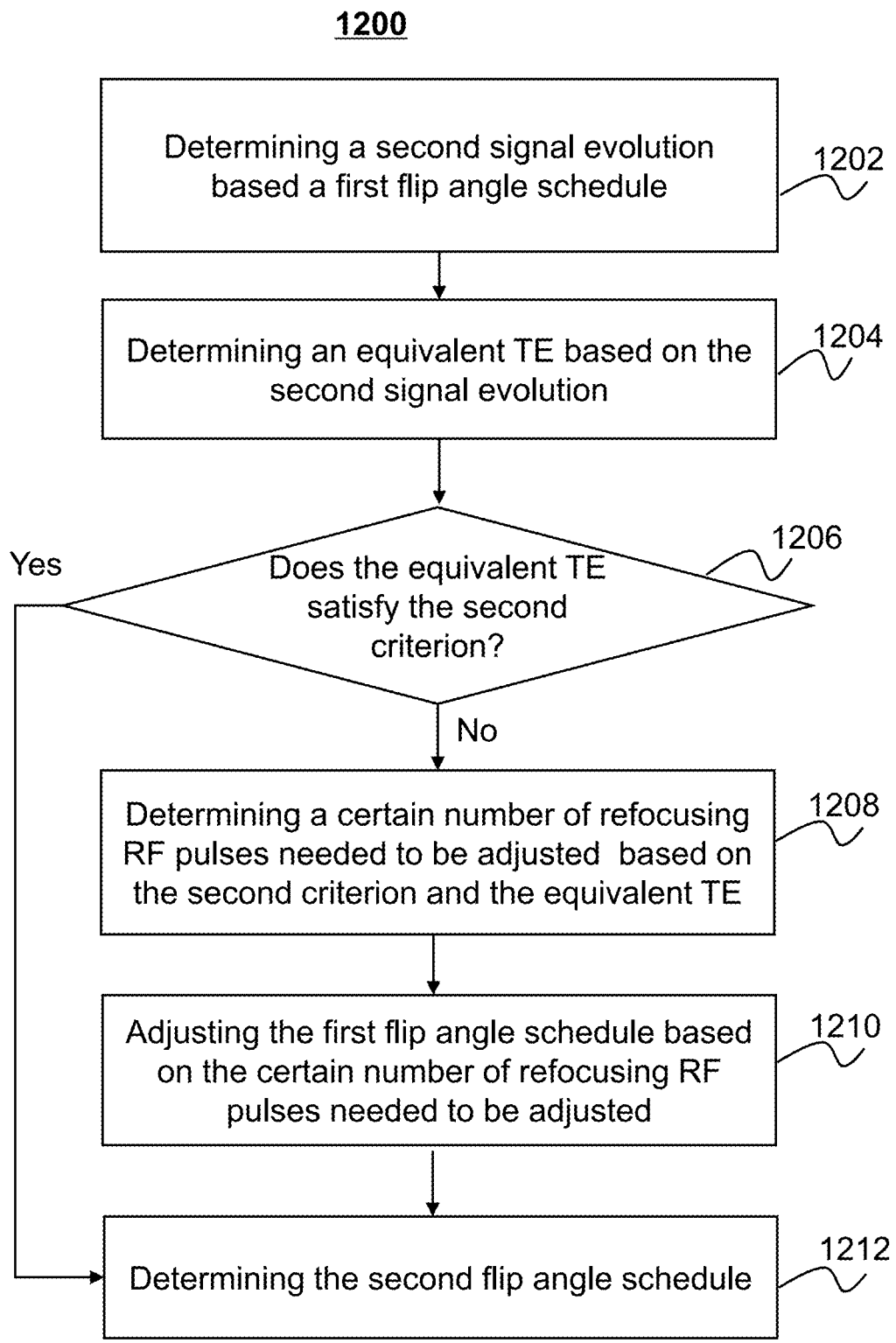
FIG. 12 is a flowchart illustrating an exemplary process for assessing a flip angle schedule according to some embodiments of the present disclosure.

FIG. 12 is a flowchart illustrating an exemplary process 1200 for assessing a first flip angle schedule according to some embodiments of the present disclosure. Operation 1008 as described in FIG. 10 may be performed according to process 1200. In some embodiments, one or more operations of process 1200 illustrated in FIG. 12 for processing an MR signal may be implemented in the MRI system 100 illustrated in FIG. 1. For example, the process 1200 illustrated in FIG. 12 may be stored in the storage device 130 in the form of instructions, and invoked and/or executed by the processing engine 120 (e.g., the processor 310 of the computing device 300 as illustrated in FIG. 3, the CPU 440 of the mobile device 400 as illustrated in FIG. 4).

In 1202, a second signal evolution corresponding to a first flip angle schedule may be determined. Operation 1202 may be performed by the calculation unit 608. In some embodiments, the first flip angle schedule may be determined as described in connection with process 1100 in FIG. 11. In some embodiments, the second signal evolution corresponding to the first flip angle schedule may include multiple signal intensities of echoes in an echo train obtained based on multiple refocusing RF pulses with the first flip angle schedule. In some embodiments, the second signal evolution may be determined based on a relationship between echoes and flip angles as described elsewhere in the disclosure. For example, the second signal evolution may be determined according to Equation (6) as illustrated in FIG. 11.

In 1204, an equivalent TE relating to the first flip angle schedule may be determined based on the second signal evolution. Operation 1202 may be performed by the calculation unit 608. As used herein, the equivalent TE relating to the first flip angle schedule may refer to an interval time from the middle of an excitation RF pulse to the middle of a refocusing RF pulse corresponding to a first center echo of the echo train obtained based on the refocusing RF pulses with the first flip angle schedule. In some embodiments, the echo with a maximum signal intensity in the second signal evolution may be designated as the first center echo. The equivalent TE relating to the first flip angle schedule may be determined based on the refocusing RF pulse corresponding to the first center echo. For example, the equivalent TE may be determined according to Equation (7) as illustrated below:

$$i = \frac{TE}{ESP}, \tag{7}$$

where i denotes the serial number of the refocusing RF pulse corresponding to the first center echo, ESP denotes a refocusing interval, also referred to as a time interval between two refocusing RF pulses. In some embodiments, the equivalent TE may be a summation of refocusing intervals before the refocusing RF pulse corresponding to the first center echo.

In 1206, a determination may be made as to whether the equivalent TE relating to the first flip angle schedule satisfies the second criterion. Operation 1206 may be performed by the assessment unit 606. In some embodiments, if the equivalent TE relating to the first flip angle schedule satisfies the second criterion, process 1200 may proceed to operation 1212. If the equivalent TE relating to the first flip angle schedule does not satisfy the second criterion, process 1200 may proceed to operation 1208. In some embodiments, the second criterion may include a third threshold relating to the equivalent TE. In some embodiments, the second criterion may be that the equivalent TE is equal to or exceeds to the third threshold. In some embodiments, the second criterion may be that a difference between the equivalent TE and the third threshold may be less than a sixth threshold (e.g., a constant).

In some embodiments, the third threshold may include a desired equivalent TE. In some embodiments, the desired equivalent TE may be set by a user via the terminal(s) 140 according to clinical demands (e.g., a type of a subject being examined). In some embodiments, the desired equivalent TE may be determined based on multiple refocusing RF pulses with a fixed flip angle schedule. For example, the multiple refocusing RF pulses with the fixed flip angle schedule may have the same flip angle equal to the flip angle of the refocusing RF pulse corresponding to the first center echo. Then, the signal intensities of echoes in an echo train obtained based on the multiple refocusing RF pulses with the fixed flip angle schedule may be determined. The echo with a maximum signal intensity may be determined to be a second center echo corresponding to the fixed flip angle schedule. The serial number of refocusing RF pulse corresponding to the second center echo may be determined. Then the desired equivalent TE may be determined, for example, according to Equation (7).

In 1208, a certain number of refocusing RF pulses needed to be adjusted may be determined based on the second criterion and the equivalent TE relating to the first flip angle schedule. Operation 1208 may be performed by the calculation unit 608. In some embodiments, the second criterion may include a desired TE, for example, the desired TE determined in 1206. Then the certain number of refocusing RF pulses needed to be adjusted may be determined based on the desired equivalent TE and the equivalent TE relating to the first flip angle schedule. For example, the certain number of refocusing RF pulses needed to be adjusted may be determined according to Equation (8) as illustrated below:

$$j = \frac{\text{desired } TE - \text{equivalent } TE}{ESP}, \quad (8)$$

where j denotes the certain number of refocusing RF pulses needed to be adjusted, and ESP denotes a refocusing interval, also refers to a time interval between two refocusing RF pulses.

In 1210, the first flip angle schedule may be adjusted based on the certain number of refocusing RF pulses needed to be adjusted. Operation 1210 may be performed by the adjustment unit 606. In some embodiments, the first flip angle schedule may be adjusted such that the equivalent TE relating to the first flip angle schedule may satisfy the second criterion, for example, the equivalent TE relating to the first flip angle schedule may be close to or equal to the desired equivalent TE. In some embodiments, the desired equivalent TE may correspond to a desired center echo (e.g., the second center echo). The first flip angle schedule may be adjusted such that the serial number of first echo center may equal the serial number of the desired center echo (e.g., the second center echo). For example, the first center echo may be the ith echo in the echo train corresponding to the ith refocusing RF pulse ($RF_i$). The desired center echo may be the (i+j)th echo in the echo train corresponding to the (i+j)th refocusing RF pulse ($RF_{i+j}$). Then the flip angles of the refocusing RF pulses from the ith to the (i+j)th may be adjusted such that the $RF_{i+j}$ may satisfy the desired center echo (e.g., the second center echo). Furthermore, the flip angles of the refocusing RF pulses from the ith to the (i+j)th may be increased monotonically such that the flip angle of the $RF_{i+j}$ may be maximum in the first flip angle schedule.

In some embodiments, the $RF_i$ and the $RF_{i+j}$ may be in different phases. For example, the first flip angle schedule may be divided into three phases including a first phase, a second phase, and a third phase. The flip angles in the first phase may decrease monotonically, the flip angles in the second phase may increase monotonically, and the flip angles in the third phase may decrease monotonically. The $RF_i$ may be located in the second phase and may be the last one refocusing RF pulse in the second phase. The $RF_{i+j}$ may be in the third phase. The flip angles of the refocusing RF pulses from the ith to the (i+j)th may be lower than the flip angle of the $RF_i$. Then the flip angles of the refocusing RF pulses from the ith to the (i+j)th may be increased monotonically to maximum the flip angle of the $RF_{i+j}$. Then, the refocusing RF pulses from the ith to the (i+j)th may be located in the second phase. The number of refocusing RF pulses in the second phase may increase and the number of refocusing RF pulses in the third phase may decrease, but the total number of refocusing RF pulses may be unchanged.

In 1212, the second flip angle schedule may be determined. Operation 1212 may be performed by the assessment unit 604. The second flip angle schedule may satisfy the second criterion. For example, the equivalent TE of an echo train obtained based on multiple refocusing RF pulses with the second flip angle schedule may be equal to or close to the third threshold (e.g., a desired equivalent TE). In some embodiments, the adjusted first flip angle schedule may be designated as the second flip angle schedule. In some embodiments, the first flip angle schedule may be designated as the second flip angle schedule if the equivalent TE corresponding to the first flip angle schedule satisfies the second criterion.

It should be noted that the above description is merely provided for purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 1210 and 1212 may be performed simultaneously. As another example, operation 1202 may be unnecessary.

EXAMPLES

The examples are provided for illustration purposes, and not intended to limit the scope of the present disclosure.

Example 1. Exemplary Flip Angle Curves

Figure 13:
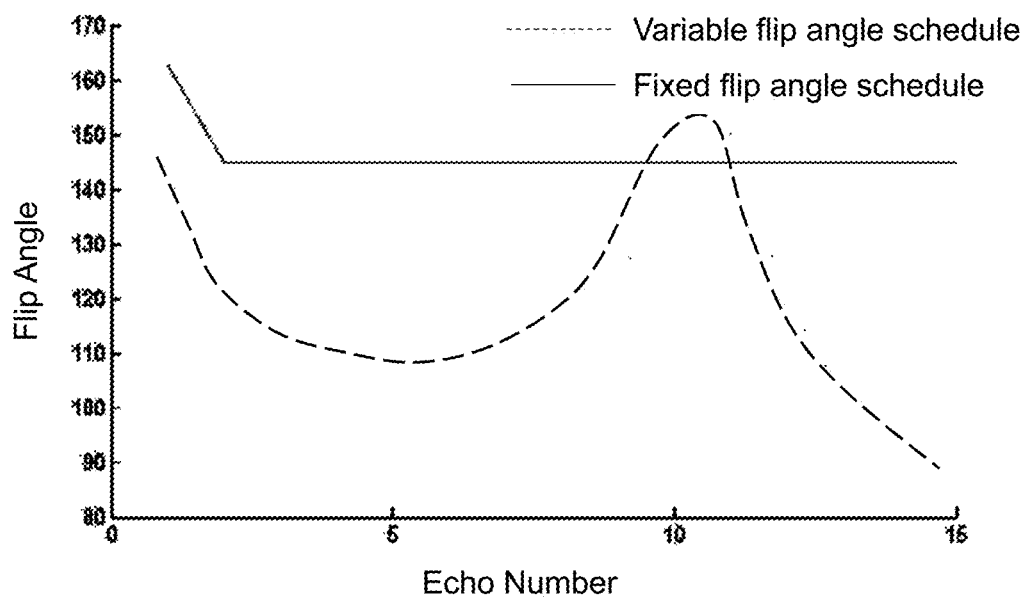
FIG. 13 illustrates exemplary curves relating to flip angles and echo numbers in echo trains according to some embodiments of the present disclosure.

FIG. 13 illustrates exemplary flip angle curves corresponding to an echo train according to some embodiments of the present disclosure. As shown in FIG. 13, the horizontal axis denotes an echo train length (ETL), also referred to as an echo number, and the vertical axis denotes a flip angle of a refocusing RF pulse. The solid curve illustrates a fixed flip angle schedule. The dotted curve illustrates a variable flip angle schedule. The fixed flip angle schedule included the same flip angle of 145°. In some embodiments, the first flip angle (also referred to as a starting flip angle) in the fixed flip angle schedule may be different from other fixed flip angles. For example, the first flip angle may be equal to a half of the sum of 90° and a fixed flip angle (e.g., 145°). The equivalent TE of the echo train corresponding to the fixed flip angle schedule was from the middle of an excitation RF pulse to the middle of the 8th refocusing RF pulse (i.e., the 8th echo). The equivalent TE of the echo train corresponding to the variable flip angle schedule was from the middle of an excitation RF pulse to the middle of the 10th refocusing RF pulse (i.e., the 10th echo). The total energy of refocusing RF pulses with the variable flip angle schedule decreased 36% relative to the total energy of refocusing RF pulses with the fixed flip angle schedule.

Example 2. Exemplary MR Images Reconstructed Based on Different Echo Trains

Figure 14A:
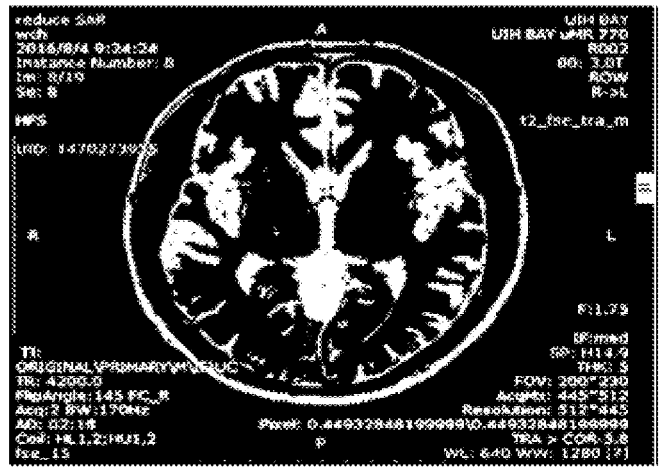
FIG. 14A and FIG. 14B illustrate exemplary MR images reconstructed based on different echo trains obtained based on different flip angle schedules according to some embodiments of the present disclosure.
Figure 14B:
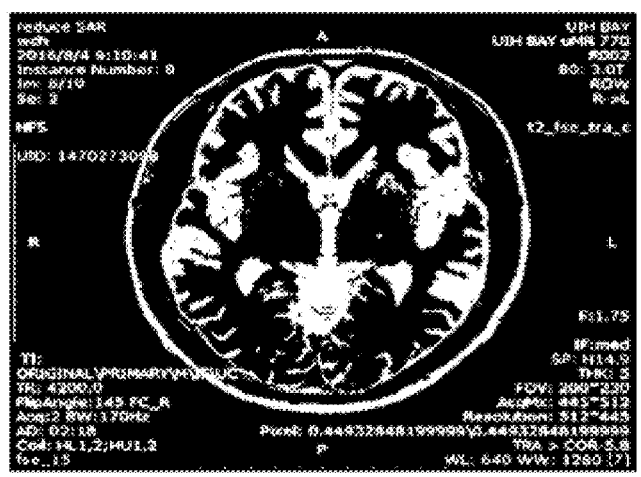

FIG. 14A and FIG. 14B illustrate exemplary MR images reconstructed based on different echo trains obtained based on different flip angle schedules according to some embodiments of the present disclosure. The image shown in FIG. 14A was generated based on MR signals obtained based on refocusing RF pulses with the fixed flip angle schedule as illustrated in FIG. 13. The image shown in FIG. 14B was generated based on MR signals obtained based on refocusing RF pulses with the variable flip angle schedule as illustrated in FIG. 13. The signal-to-noise ratio and the contrast ratio of the images shown in FIG. 14B and FIG. 14A were similar even though the total energy of refocusing RF pulses with the variable flip angle schedule decreased 36% relative to the total energy of refocusing RF pulses with the fixed flip angle schedule as illustrated in FIG. 13.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing device having at least one processor, at least one computer-readable storage medium, and a communication port connected to an imaging device, the method comprising:
    providing an initial flip angle schedule of refocusing radio frequency pulses, the refocusing radio frequency pulses being configured to generate an echo train;
    performing an iterative process comprising, for each iteration of the iterative process,
        comparing the initial flip angle schedule with a first criterion, the first criterion relating to a first parameter relating to the echo train;
        in response to a determination that the initial flip angle schedule fails to satisfy the first criterion, determining a first flip angle schedule, the first flip angle schedule satisfying the first criterion;
        comparing the first flip angle schedule with a second criterion, the second criterion relating to a second parameter relating to the echo train;
        in response to a determination that the first flip angle schedule fails to satisfy the second criterion,
            determining, based on the first flip angle schedule, a second flip angle schedule, the second flip angle schedule satisfying the second criterion; and
            updating the initial flip angle schedule using the second flip angle schedule;
    designating the first flip angle schedule as a target flip angle schedule responsive to terminating the iterative process when the first flip angle schedule satisfies the second criterion; and
    obtaining, based on the target flip angle schedule, a magnetic resonance (MR) signal.

2. The method of claim 1, wherein the providing the initial flip angle schedule of the refocusing radio frequency pulses comprises:
    selecting an initial condition relating to the refocusing radio frequency pulses, the initial condition including initial values of a first flip angle and a second flip angle; and
    determining the initial flip angle schedule based on the initial values of the first flip angle and the second flip angle.

3. The method of claim 2, further comprising:
    providing a function corresponding to at least a portion of the echo train, the function relating to at least one of the first flip angle and the second flip angle; and
    determining, based on the function, at least one flip angle of at least one refocusing radio frequency pulse, a flip angle of the at least one refocusing radio frequency pulse corresponding to an echo in the echo train.

4. The method of claim 1, wherein the first parameter relating to the echo train includes an intensity value of at least one echo in the echo train.

5. The method of claim 1, wherein the determining a first flip angle schedule, further comprises:
    adjusting the initial flip angle schedule to determine the first flip angle schedule.

6. The method of claim 1, wherein the determination that the initial flip angle schedule fails to satisfy a first criterion comprises:
    determining, based on the initial flip angle schedule, a first signal evolution; and
    determining that the initial flip angle schedule does not satisfy the first criterion by determining that the first signal evolution does not satisfy the first criterion, wherein the first signal evolution includes intensity values of at least a portion of echoes in the echo train.

7. The method of claim 6, wherein the first signal evolution relates to at least one of a transverse relaxation time or a longitudinal relaxation time.

8. The method of claim 6, wherein the first criterion includes a threshold corresponding to the first signal evolution, and the determining that the initial flip angle schedule does not satisfy a first criterion includes determining that a maximum intensity value in the first signal evolution is lower than the threshold corresponding to the first signal evolution.

9. The method of claim 1, wherein the first parameter relating to the echo train includes a total energy of the refocusing radio frequency pulses associated with the initial flip angel schedule.

10. The method of claim 9, wherein the determination that the initial flip angle schedule fails to satisfy a first criterion comprises:
    determining, based on the initial flip angle schedule, the total energy of the refocusing radio frequency pulses; and
    determining that the initial flip angle schedule fails to satisfy a first criterion by evaluating the total energy of the refocusing radio frequency pulses according to the first criterion.

11. The method of claim 10, wherein the first criterion includes a threshold corresponding to the total energy of the refocusing radio frequency pulses, and the determining that the initial flip angle schedule does not satisfy a first criterion includes determining that the total energy of the refocusing radio frequency pulses equals to or exceeds the threshold corresponding to the total energy of the refocusing radio frequency pulses.

12. The method of claim 1, wherein the determining based on the first flip angle schedule, a second flip angle schedule, further comprises:
    adjusting the first flip angle schedule to determine the second flip angle schedule.

13. The method of claim 1, wherein the second parameter includes an equivalent echo time of the echo train corresponding to the first flip angle schedule.

14. The method of claim 13, wherein the second criterion includes a threshold corresponding to the equivalent echo time of the echo train corresponding to the first flip angle schedule.

15. The method of claim 14, wherein the determination that the first flip angle schedule fails to satisfy a second criterion comprises:
   determining a second signal evolution, the second signal evolution including intensity values of at least a portion of echoes in the echo train corresponding to the first flip angle schedule;
   determining, based on the second signal evolution, the equivalent echo time of the echo train corresponding to the first flip angle schedule; and
   determining that the first flip angle schedule fails to satisfy the second criterion by determining that the equivalent echo time of the echo train corresponding to the first flip angle schedule fails to satisfy the second criterion.

16. The method of claim 15, wherein the determining that the first flip angle schedule does not satisfy the second criterion comprises determining that the equivalent echo time of the echo train corresponding to the first flip angle schedule is lower than threshold corresponding to the equivalent echo time of the echo train.

17. A system, comprising:
   at least one processor; and
   executable instructions, the executable instructions being executed by the at least one processor, causing the system to implement a method, comprising:
      providing an initial flip angle schedule of refocusing radio frequency pulses, the refocusing radio frequency pulses being configured to generate an echo train;
      performing an iterative process comprising, for each iteration of the iterative process,
      comparing the initial flip angle schedule with a first criterion, the first criterion relating to a first parameter relating to the echo train;
      in response to a determination that the initial flip angle schedule fails to satisfy the first criterion, determining a first flip angle schedule, the first flip angle schedule satisfying the first criterion;
      comparing the first flip angle schedule with a second criterion, the second criterion relating to a second parameter relating to the echo train;
      in response to a determination that the first flip angle schedule fails to satisfy the second criterion,
         determining, based on the first flip angle schedule, a second flip angle schedule, the second flip angle schedule satisfying the second criterion; and
         updating the initial flip angle schedule using the second flip angle schedule;
      designating the first flop angle schedule as a target flip angle schedule responsive to terminating the iterative process when the first flip angle schedule satisfies the second criterion; and
      obtaining, based on the target flip angle schedule, a magnetic resonance (MR) signal.

18. The system of claim 17, wherein the first parameter relating to the echo train includes at least one of an intensity value of at least one echo in the echo train or a total energy of the refocusing radio frequency pulses associated with the initial flip angel schedule.

19. The system of claim 17, wherein the second parameter includes an equivalent echo time of the echo train corresponding to the first flip angle schedule.

20. A non-transitory computer readable medium, comprising:
   instructions being executed by at least one processor, causing the at least one processor to implement a method, comprising:
      performing an iterative process comprising, for each iteration of the iterative process,
      comparing the initial flip angle schedule with a first criterion, the first criterion relating to a first parameter relating to the echo train;
      in response to a determination that the initial flip angle schedule fails to satisfy the first criterion, determining a first flip angle schedule, the first flip angle schedule satisfying the first criterion;
      comparing the first flip angle schedule with a second criterion, the second criterion relating to a second parameter relating to the echo train;
      in response to a determination that the first flip angle schedule fails to satisfy the second criterion,
         determining, based on the first flip angle schedule, a second flip angle schedule, the second flip angle schedule satisfying the second criterion; and
         updating the initial flip angle schedule using the second flip angle schedule:
      designating the first flit angle schedule as a target flin angle schedule responsive to terminating the iterative process when the first flip angle schedule satisfies the second criterion; and
   obtaining, based on the second-target flip angle schedule, a magnetic resonance (MR) signal.

* * * * *